(12) United States Patent
Yaghi et al.

(10) Patent No.: US 7,582,798 B2
(45) Date of Patent: Sep. 1, 2009

(54) COVALENTLY LINKED ORGANIC FRAMEWORKS AND POLYHEDRA

(75) Inventors: Omar M. Yaghi, Los Angeles, CA (US); Adam J. Matzger, Ann Arbor, MI (US); Annabelle Benin, Oak Forest, IL (US); Adrien P. Côte, Mississauga (CA)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/256,859

(22) Filed: Oct. 24, 2005

(65) Prior Publication Data

US 2006/0154807 A1    Jul. 13, 2006

Related U.S. Application Data

(60) Provisional application No. 60/621,410, filed on Oct. 22, 2004.

(51) Int. Cl.
   *C07F 5/02*    (2006.01)
(52) U.S. Cl. .......................................................... 568/3
(58) Field of Classification Search ................... 502/150
   See application file for complete search history.

(56) References Cited

U.S. PATENT DOCUMENTS

| | | | |
|---|---|---|---|
| 3,144,418 A | 8/1964 | Hill et al. |
| 4,359,327 A | 11/1982 | Armand et al. |
| 5,616,650 A | 4/1997 | Becker et al. |
| 5,629,523 A | 5/1997 | Ngo et al. |
| 5,648,508 A | 7/1997 | Yaghi |
| RE35,908 E | 9/1998 | Kitaguchi et al. |
| 5,862,796 A | 1/1999 | Seki et al. |
| 5,880,471 A | 3/1999 | Schelten et al. |
| 5,940,460 A | 8/1999 | Seidel et al. |
| 6,072,181 A | 6/2000 | Hassard et al. |
| 6,312,902 B1 | 11/2001 | Shultz et al. |
| 6,348,607 B1 | 2/2002 | Muller et al. |
| 6,479,680 B1 | 11/2002 | Bassler et al. |
| 6,479,826 B1 | 11/2002 | Klann et al. |
| 6,518,441 B2 | 2/2003 | Grosch et al. |
| 6,545,281 B1 | 4/2003 | McGregor et al. |
| 6,617,467 B1 | 9/2003 | Mueller et al. |
| 6,624,318 B1 | 9/2003 | Mueller et al. |
| 6,727,371 B2 | 4/2004 | Muller et al. |
| 6,893,564 B2 | 5/2005 | Mueller et al. |
| 6,929,679 B2 | 8/2005 | Muller et al. |
| 6,930,193 B2 | 8/2005 | Yaghi et al. |
| 6,965,026 B2 | 11/2005 | Zaworotko et al. |
| 7,008,607 B2 | 3/2006 | Muller et al. |
| 7,119,219 B2 | 10/2006 | Muller et al. |
| 2003/0078311 A1 | 4/2003 | Muller et al. |
| 2004/0110950 A1 | 6/2004 | Li et al. |
| 2004/0225134 A1 | 11/2004 | Yaghi et al. |
| 2004/0265670 A1 | 12/2004 | Mueller et al. |

FOREIGN PATENT DOCUMENTS

| | | |
|---|---|---|
| CA | 2 387 122 | 2/2001 |
| CA | 2 414 756 | 1/2003 |
| CA | 2 414 779 | 1/2003 |
| DE | 44 08 772 | 9/1994 |
| DE | 197 23 950 | 12/1998 |
| DE | 198 35 907 | 2/2000 |
| DE | 198 47 629 | 4/2000 |
| DE | 199 36 547 | 2/2001 |
| DE | 100 15 246 | 10/2001 |
| DE | 100 32 884 | 1/2002 |
| DE | 100 32 885 | 1/2002 |
| DE | 101 11 230 | 9/2002 |
| DE | 101 43 195 | 3/2003 |
| EP | 00 557 116 | 8/1993 |
| EP | 0 727 608 | 8/1996 |
| EP | 0 790 253 | 8/1997 |
| EP | 1 280 090 A1 | 1/2003 |
| JP | 2004024247 | 1/2004 |
| WO | WO 97/46711 | 12/1997 |
| WO | WO 99/05151 | 2/1999 |
| WO | WO 00/78837 | 12/2000 |
| WO | WO 01/16209 | 3/2001 |
| WO | WO 01/27186 | 4/2001 |
| WO | WO 02/070526 | 9/2002 |
| WO | WO 02/088148 | 11/2002 |
| WO | WO 03/035717 | 5/2003 |
| WO | WO 03/044228 A1 | 5/2003 |

OTHER PUBLICATIONS

Glybin et al., {Standard enthalpies of formation of mononuclear and cluster oxoanions of boron, silicon, and phosphorus, Zhurnal Fizicheskoi Khimii (2000), 74(6), 974-979}.*
Warren et al., {A bimetallic main group oxide cluster of the oxovanadium borate system: (H3NCH2CH2NH3)4[(VO)12O4{B8O17(OH)4}2{Mn(H2O)2}2]-H2O, Inorganica Chimica Acta (1998), 282(1), 123-129).*
Choudhury et al., {An open-framework zincoborate formed by Zn6B12O24 clusters, Journal of the Chemical Society, Dalton Transactions, (2002), (7), 1535-1538}.*
Grimes, {Boron clusters come of age, Journal of Chemical Education (2004), 81(5), 657-672}.*
U.S. Appl. No. 10/270,642, filed Oct. 16, 2002, Mueller et al.

*Primary Examiner*—Sikarl A. Witherspoon
*Assistant Examiner*—Chukwuma O Nwaonicha
(74) *Attorney, Agent, or Firm*—Brooks Kushman P.C.

(57) ABSTRACT

A covalently linked organic network includes a plurality of boron-containing clusters linked together by a plurality of linking groups. The covalently linked organic networks are characterized by having each linking group bonded to at least two distinct boron-containing clusters.

12 Claims, 11 Drawing Sheets

OTHER PUBLICATIONS

U.S. Appl. No. 10/611,863, filed Jul. 3, 2003, Mueller et al.
U.S. Appl. No. 10/983,629, filed Nov. 9, 2004, Hesse et al.
Bondi, A., "van der Waals Volumes and Radii," Journal of Phys. Chem., Mar. 16, 1994, vol. 68, No. 3, pp. 441-451.
Bennett, J.M. and J.V. Smith, "Positions of Cations and Molecules in Zeolites with the Faujastie-Type Framework I. Dehydrated Ca-Exchanged Faujasite," Mat. Res. Bull., vol. 3, No. 8, 1968, pp. 633-642.
Hoskins, B.F. and R. Robson, "Infinite Polymeric Frameworks Consisting of Three Dimensionally Linked Rod-Like Segments", J. Am. Chem. Soc., 1989, vol. 111, pp. 5962-5964.
Fagan, P.J. and M.D. Ward, "Building Molecular Crystals," Sci. Am., Jul. 1992, pp. 48-54.
Stein, A., S.W. Keller and T.E. Mallouk, "Turning Down Heat, Design and Mechanism in Solid-State Synthesis," Mar. 12, 1993, vol. 259, pp. 1558-1564.
Russell, V.A., C.C. Evans, W.Li and M.D. Ward, "Nanoporous Molecular Sandwiches: Pillared Two-Dimensional Hydrogen-Bonded Networks with Adjustable Porosity," Science, Apr. 25, 1997, vol. 276, pp. 575-579.
Husing, N. and U. Schubert, "Aerogels-Airy Materials: Chemistry, Structure, and Properties," Agnew. Chem. Int. Ed., 1998, vol. 37, pp. 22-45.
Menon, V.C. and S. Komarneni, "Porous Adsorbents for Vehicular Natural Gas Storage: A Review," J. of Porous Materials, 1998, vol. 5, pp. 43-58.
Jones, C.W., K. Tsuji and M.E. Davis, "Organic-Functionalized Molecular Sieves as Shape-Selective Catalysts," Nature, May 7, 1998, vol. 393, pp. 52-54.
Fujita, M. "Self-Assembly of [2]Catenanes Containing Metals in Their Backbones," Accounts of Chemical Research, 1999, vol. 32, No. 1, pp. 53-61.
Li, H., M. Eddaoudi, M. O'Keeffe and O.M. Yaghi, "Design and Synthesis of an Exceptionally Stable and Highly Porous Metal-Organic Framework," Nature, Nov. 18, 1999, vol. 402, pp. 276-279.
Li, H., C.E. Davis, T.L. Groy, D.G. Kelley and O.M. Yaghi, Coordinately Unsaturated Metal Centers in the Extended Porous Framework of $Zn_3$ $(BDC)_3 6CH_3OH$ (BDC = 1,4-Benzenedicarboxylate), J. Am. Chem. Soc., 1998, vol. 120, pp. 2186-1287.
Kiang, Y.-H. G.B. Gardner, S. Lee, Z. Xu and E.B. Lobkovsky, "Variable Pore Size, Variable Chemical Functionality, and an Example of Reactivity Within Porous Phenylacetylene Silver Salts," J. Am. Chem. Soc., 1999, vol. 121, pp. 8204-8215.
Eddaoudi, M., H. Li and O.M. Yaghi, "Highly Porous and Stable Metal-Organic Frameworks: Structure Design and Sorption Properties," J. Am. Chem. Soc., 2000, vol. 122, pp. 1391-1397.
Noro, S., S. Kitagawa, M. Kondo and K. Seki, "A New, Methane Adsorbent, POrous Coordination Polymer [{$CuSiF_6$(4,4-bipyridine)$_2$}$_n$]," Angew. Chem. Int. Ed., 2000, vol. 39, No. 12, pp. 2081-2084.
Yaghi, O.M., M. O'Keeffe and M. Kanatzidis, "Design of Solids from Molecular Building Blocks: Golden Opportunities for Solid State Chemistry," J. Solid State Chem., 2000, vol. 152, pp. 1-2.
Reineke, T.M., M. Eddaoudi, D. Moler, M. O'Keeffe and O.M. Yaghi, "Large Free Volume in Maximally Interpenetrating Networks: The Role of Secondary Building Units Exemplified by $Tb_2(ADB)_2[CH_{32}SO]_4 16[(CH_3)_2SO]^1$," J. Am. Chem. Soc., 2000, vol. 122, pp. 4843-4844.
Eddaoudi, M., D.B., Moler, H. Li, B. Chen, T.M. Reineke, M. O'Keeffe and O.M. Yaghi, "Modular Chemistry: Secondary Building Units as a Basis for the Design of Highly Porous and Robust Metal-Organic Carboxylate Frameworks," Acc. Chem. Res., 2001, vol. 34, pp. 319-330.
Seki, K., "Design of an Adsorbent with an Ideal Fore Structure for Methane Adsorption Using Metal Complexes," Chem. Commun., 2001, 1496-1497.
Kim, J., B. Chen, T.M. Reinke, H. Li, M. Eddaoudi, D.B. Moler, M. O'Keeffe and O.M. Yaghi, "Assembly of Metal-Organic Frameworks from Large Organic and Inorganic Secondary Building Units: New Examples and Simplifying Principles for Complex Structures," J. Am. Chem. Soc., 2001, vol. 123, pp. 8239-8274.
Guillou, N., Q. Gao, P.M. Forster, J. Chang, M. Norgues, S. Park, G. Ferey and A. K. Cheetham, "Nickel(ii) Phosphate VSB-5: A Magnetic Nanoporous Hydrogenation Catalyst with 24-Ring Tunnels," Angew. Chem. Int. Ed., 2001, vol. 40, No. 15, pp. 2831-2834.
Naumov, P., G. Jovanovski, M. Ristova, I.A. Razak, S. Cakir, S. Chantrapromma, H. Fun and S. Weng NG, "Coordination of Deprotonated Saccharin in Copper(II) Complexes. Structural Role of the Saccharinate Directed by the Ancillary N-heterocyclic Ligands," Z. Anorg. Allg. Chem., 2002, vol. 628, pp. 2930-2939.
Wallner, H. and K. Gatterer, "Growth of Pure $Ni(OH)_2$ Single Crystals from Solution—Control of the Crystal Size," Z. Anorg. Allg. Chem., 2002, vol. 628, pp. 2818-2820.
Patoux, S. and C. Masquelier, "Lithium Insertion into Titanium Phosphates, Silicates and Sulfates," Chemistry of Materials, 2002, vol. 14, No. 12, pp. 5057-5068.
Rosi, N., M. Eddaoudi, J. Kim et al., "Infinite Secondary Building Units & Forbidden Catenation in Metal-Organic Frameworks", Angew. Chem. Int. Ed., 2002, 41, No. 2, pp. 284-285.
Eddaoudi, M., J. Kim, N. Rosi et al., "Systematic Design of Pore Size & Functionality in Isoreticular MOFs & Their Application in Methane Storage", Science, vol. 295, Jan. 18, 2002, pp. 469-472.
Seki, K., "Surface Area Evaluation of Coordination Polymers Having Rectangular Micropores", Langmuir 2002, 18, pp. 2441-2443.
Seki, K. and W. Mori, "Syntheses & Characterization of Microporous Coordination Polymers with Open Frameworks", J. Phys. Chem. B, 2002, 106, pp. 1380-1385.
Rosi, N.L., J. Eckert, M. Eddaoudi et al., "Hydrogen Storage in Microporous Metal-Organic Frameworks", Science, vol. 300, May 16, 2003, pp. 1127-1129.
Yaghi, O.M., M. O'Keeffe, N.W. Ockwig et al., "Reticular Synthesis and the Design of New Materials", Nature, vol. 423, Jun. 2003, pp. 705-714.
McGregor, Douglas S. et al., "Semi-Insulating Bulk GaAs Thermal Neutron Imaging Arrays," IEEE Transactions on Nuclear Science, vol. 43, No. 3, Jun. 1996, pp. 1357-1364.
Rose, A., "Sputtered Boron Films on Silicon Surface Barrier Detectors," Nuclear Instruments and Methods, 52, 1967, pp. 166-170.
Feigl, B. et al., "Der Gd-Neutronenzahler," Nuclear Instruments and Methods, 61, Wien, Austria, 1968, pp. 349-356.
Mireshghi, A. et al., "High Efficiency Neutron Sensitive Amorphous Silicon Pixel Detectors," IEEE Transactions on Nuclear Science, vol. 41, No. 4, Aug. 1994, pp. 915-921.
Foulon, F. et al., "Neutron Detectors Made From Chemically Vapour Deposited Semiconductors," Proc. MRS. 487, 1998, pp. 591-596.
Dulloo, A.R. et al., "Radiation Response Testing of Silicon Carbide Semiconductor Neutron Detectors for Monitoring Thermal Neutron Flux," Report 97-9TK1-NUSIC-R1, Westinghouse STC, Pittsburgh, PA, Nov. 18, 1997, pp. 6-1-6-14.
Knoll, Glenn F., Radiation Detection and Measurement, 3rd Ed. John Wiley & Sons, Inc., New York, 2000, Chapter 14, pp. 505-508.
Garber, D.I. et al., "Neutron Cross Sections," 3rd Edition, vol. 11, Curves, Brookhaven National Laboratory, Upton, Jan. 1976, pp. 11-13 & pp. 23-24.
McLane, Victoria et al., "Neutron Cross Sections," vol. 2, Neutron Cross Section Curves, Academic Press, San Diego, CA, 1988, pp. 12-13 & pp. 26-27.
McGregor, Douglas, S.et al., "Thin-Film-Coated Bulk GaAs Detectors for Thermal and Fast Neutron Measurements," Nuclear Instruments and Methods in Physics Research A 466, 2001, pp. 126-141.
McGergor, Douglas, S. et al., "Design Considerations for Thin Film Coated Semiconductor Thermal Neutron Detectors—I: Basics Regarding Alpha Particle Emitting Neutron Reactive Films," Nuclear Instruments & Methods, A 500, 2003, pp. 272-308.
Puckett, P.R. et al., "Thin Film Processes II," Chapter V-2, J.L. Vossen and W. Kern, Eds., Academic Press, Boston, 1991, pp. 749, 768-770.
Sze, S.M., "VLSI Technology," McGraw-Hill, New York, 1983.
Ruska, W.S., "Microelectronic Processing," McGraw-Hill, New York, 1987.
McGregor, Douglas, S. et al., "Self-Biased Boron-10 Coated High-Purity Epitaxial GaAs Thermal Neutron Detectors," IEEE Transactions on Nuclear Science, vol. 47, No. 4, Aug. 2000, pp. 1364-1370.

Klann, Raymond T. et al., "Development of Coated Gallium Arsenide Neutron Detectors," Conference Record of ICONE-8, 8TH International Conf. on Nuclear Eng., Apr. 2-6, 2000, Baltimore, MD, pp. 1-6.

McGregor, Douglas, S. et al., "New Surface Morphology for Low Stress Thin-Film-Coated Thermal Neutron Detectors," IEE Transactions on Nuclear Science, vol. 49, No. 4, Aug. 2002, pp. 1999-2004.

http://www.mems-exchange.org/.

http://physics.nist.gov/MajResProj/rfcell/drawings.html.

Schelten, J. et al., "A New Neutron Detector Development Based on Silicon Semiconductor and LiF Converter," Physica B 234-236, 1997, pp. 1084-1086.

Atomnaya Energiya, Soviet Atomic energy, Russian Original, vol. 62, No. 4, Apr. 1987, pp. 316-319.

Allier, C.P., "Micromachined Si-Well Scintillator Pixel Detectors," Chapter 8, 2001, pp. 122-134.

McGregor, Douglas S. et al., "Bulk GaAs-Based Neutron Detectors for Spent Fuel Analysis," Proceedings of ICONE 8, 8th Int'l Conf. on Nuclear Eng., Baltimore, MD, Apr. 2-6, 2000, pp. 1-5.

De Lurgio, Patrick M. et al., "A Neutron Detector To Monitor the Intensity of Transmitted Neutrons for Small-Angle Neutron Scattering Instruments," Elsevier Science B.V., Nuclear Instruments and Methods in Physics Research A 505, 2003, pp. 46-49.

Klann, Raymond T. et al., "Development of Semiconductor Detectors For Fast Neutron Radiography," 15th Int'l. conf. on Applications of Accelerators in Research and Industry, Nov. 2000, pp. 1-4.

Gersch, H.K. et al., "The Effect of Incremental Gamma-Ray Doses and Incremental Neutron Fluences Upon the Performance of Self-Biased.10B-Coated High-Purity Epitaxial GaAs Thermal Neutron Detectors," Nuclear Instruments and Methods in Physics Research A 489, Feb. 12, 2002, pp. 85-98.

McGregor, Douglas S. et al., "Thin-Film-Coated Detectors For Neutron Detection," J. Of Korean Assoc. For Radiation Protection, vol. 26, 2001, pp. 167-175.

McGregor, Douglas, S. et al., "Designs For Thin-Film-Coated Semiconductor Thermal Neutron Detectors," University of Michigan, Ann Arbor, Michigan, Nov. 14, 2001, pp. 1-6.

McGregor, Douglas S. et al., "Recent Results From Thin-Film-Coated Semiconductor Neutron Detectors," Proceedings of SPIE, vol. 4784, 2002, pp. 164-182.

Chae et al ., "A route to high surface area, porosity and inclusion of large molecules in crystals," Nature, 2004, vol. 427, pp. 523-527.

Eddaoudi, M., J. Kim, J. B. Wachter et al., "Porous Metal-Organic Polyhedra: 25Å Cuboctahedron Constructed from 12 $CU_2$ $(CO_2)_4$ Paddle-Wheel Building Blocks," J. Am. Chem. Soc., 2001, 123, pp. 4368-4369.

Biradha, K., Y. Hongo & M. Fujita, "Open Square-Grid Coordination Polymers of the Dimension 20×20 Å: Remarkably Stable & Crystalline Solids Even After Guest Removal," Angew. Chem. Int. Ed., 2000, 39, No. 21, pp. 3843-3845.

Li, Hailian, C.E. Davis, T.L. Grow, D.G. Kelley, O.M. Yaghi, "Coordinatively Unsaturated Metal Centers in the Extended Porous Framework of $Zn_3(BDC)_3 6CH_3OH$ (BDC=1,4-Benzenedicarboxylate)," J. Am. Chem. Soc. 1998, 120, pp. 2186-2187.

Yaghi, O.M., G. Li, H. Li, "Selective binding and removal of guests in a microporous metal-organic framework," Nature, vol. 378(6558), Dec. 14, 1996, pp. 703-706.

Yaghi, O.M., C.E. Davis, G. Li, and H. Li, "Selective Guest Binding by Tailored Channels in a 3-D Porous Zinc(II)-Benzenetricarboxylate Network," J. Am. Chem. Soc. 1997, 199, pp. 2861-2868.

Yaghi, O.M., H. Li, "Hydrothermal Synthesis of a Metal-Organic Framework Containing Large Rectangular Channels," J. Am. Chem. Soc. 1995, 117, pp. 10401-10402.

Yaghi, O.M., H. Li, C. Davis, D. Richardson and T.L. Groy, "Synthetic Strategies, Structure Patterns, and Emerging Properties in the Chemistry of Modular Porous Solids," Acc. Chem. Res. 1998, 31, pp. 474-484.

Li, H., M. Eddaoudi, D.A. Richardson, and O.M. Yaghi, Porous Germanates: Synthesis, Strucuture, and Inclusion Properties of $Ge_7O_{14.5}F_2 \cdot [(CH_3)_2NH_2]_3(H_2O)_{0.86}$, J. Am. Chem. Soc., 1998, 120, pp. 8567-8568.

Li, H., M. Eddaoudi, T.L. Groy and O.M. Yaghi, Establishing Microporosity in Open Metal—Organic Frameworks: Gas Sorption Isotherms for Zn(BDC) (BDC = 1,4-Benzenedicarboxylate), J. Am Chem. Soc. 1998, 120, pp. 8571-8572.

Li, H. and O.M. Yaghi, "Transformation of Germanium Dioxide to Microporous Germanate 4-Connected Nets," J. Am. Chem. Soc. 1998, 120, pp. 10569-10570.

Reineke, T.M., M. Eddaoudi, M. Fehr, D. Kelley and O.M. Yaghi, "From Condensed Lanthanide Coordination Solids to Microporous Frameworks Having Accessible Metal Sites," J. Am. Chem. Soc. 1999, 121, pp. 1651-1657.

Li, H., M. Eddaoudi, and O.M. Yaghi, "An Open-Framework Germanate with Polycubane-Like Topology," Angew. Chem. Int. Ed. 1999, 38, No. 5, pp. 653-655.

Reineke, T., M. Eddaoudi, M. O'Keeffe and O. M. Yaghi, "A Microporous Lanthanide—Organic Framework," Angew. Chem. Int. Ed. 1999, 38, No. 17, pp. 2590-2594.

Chen, B., M. Eddaoudi, T.M. Reineke, J.W. Kampf, M. O'Keeffe and O.M. Yaghi, $CU_2(ATC) \cdot (6H_2O)$: Design of Open Metal Sites in Porous Metal-Organic Crystals (ATC: 1,3,5,7-Adamantane Tetracarboxylate), J. Am. Chem. Soc. 2000, 122, pp. 11559-11560.

Chae, H.K., M. Eddaoudi, J. Kim, S.I. Hauck, J.F. Hartwig, M. O'Keeffe and O.M. Yaghi, "Tertiary Building Units: Synthesis, Structure, and Porosity of a Metal-Organic Dendrimer Framework (MODF-1)," J. Am. Chem. Soc. 2001, 123, pp. 11482-11483.

Braun, M.E., C.D. Steffek, J. Kim, P.G. Rasmussen and O.M. Yaghi, "1,4-Benzenedicarboxylate derivatives as links in the design of paddle-wheel units and metal-organic frameworks," Chem. Commun., 2001, pp. 2532-2533.

Barton, T.J., L.M. Bull, W.G. Klemperer, D.A. Loy, B. McEnaney, M. Misono, P.A. Monson, G. Pez, G.W. Scherer, J.C. Vartuli and O.M. Yaghi, "Tailored Porous Materials," Chem. Mater. 1999, 11, pp. 2633-2656.

Eddaoudi, M., J. Kim, M. O'Keeffe and O.M. Yaghi, "$Cu_2[o$-$Br$-$C_6H_3(CO_2)_2]_2(H_2O)_2(DMF)_8(H_2O)_2$: A Framework Deliberately Designed To Have the NbO Structure Type," J. Am. Chem. Soc., 2002, vol. 124, No. 3, pp. 376-377.

Rosi, N.L., M. Eddaoudi, J. Kim, M. O'Keeffe and O.M. Yaghi, "Advances in the chemistry of metal-organic frameworks," CrystEngComm, 2002, 4(68), pp. 401-404.

Plevert, J., R. Sanchez-Smith, T.M. Gentz, H. Li, T.L. Groy, O.M. Yaghi and M. O'Keeffe, "Synthesis and Characterization of Zirconogermanates," Inorganic Chemistry, vol. 42, No. 19, 2003, pp. 5954-5959.

Vodak, D.T., K. Kim, L. Iordanidis, P.G. Rasmussen, A.J. Matzger and O.M. Yaghi, "Computation of Aromatic $C_3N_4$ Networks and Synthesis of the Molecular Precursor $N(C_3N_3)_3CL_6$," Chem. Eur. J. 2003, 9, pp. 4197-4201.

Olaf Delgado Friedrichs, Michael O'Keeffe and Omar M. Yaghi, "Three-periodic nets and tilings: regular and quasiregular nets," Acat Cryst., 2003, A59, pp. 22-27.

Olaf Delgado Friedrichs, Michael O'Keeffe and Omar M. Yaghi, "Three-periodic nets and tilings: semiregular nets," Acat Cryst., 2003, A59, pp. 515-525.

Hailian Li, Jaheon Kim, Michael O'Keeffe and Omar M. Yaghi, "$[Cd_{16}In_{64}S_{134}]^{44-}$: 31-Å Tetrahedron with a Large Cavity," Angew. Chem. Int. Ed., 2003, 42, pp. 1819-1821.

Chae, H.K., J. Kim, O.D. Friedrichs, M. O'Keeffe and O.M. Yaghi, "Design of Frameworks with Mixed Triangular and Octahedral Building Blocks Exemplified by the Structure of $[Zn_4O(TCA)_2]$ Having the Pyrite Topoylogy," Angew. Chem. Int. Ed, 2003, 42, pp. 3907-3909.

Plevert, J., T.M. Gentz, T.L. Groy, M. O'Keeffe and O.M. Yaghi, "Layered Structures Constructed from New Linkages of $Ge_7(O,OH,F)19$ Clusters," Chem. Mater., 2003, 15, pp. 714-718.

Duren, T., L. Sarkisov, O.M. Yaghi and R.Q. Snurr, "Design of New Materials for Methane Storage," Langmuir, 2004, 20, pp. 2683-2689.

Rowsell, J.L.C., A.R. Millward, K.S. Park and O.M. Yaghi, "Hydrogen Sorption in Functionalized Metal-Organic Frameworks," J. Am. Chem. Soc., 2004, 126, pp. 5666-5667.

Rowsell, J.L.C., O.M. Yaghi, "Metal-organic frameworks: a new class of porous materials," Microporous and Mesoporous Materials 73 (2004), pp. 3-14.

Rosi, N.L., J. Kim, M. Eddaoudi, B. Chen, M. O'Keeffe and O.M. Yaghi, "Rod Packings and Metal-Organic Frameworks Constructed from Rod-Shaped Secondary Building Units," J. Am. Chem. Soc., 2005, 127, pp. 1504-1518.

Chen, B., N.W. Ockwig, F.R. Fronczek, D.S. Contreras and O.M. Yaghi, "Transformation of a Metal-Organic Framework from the NbO to PtS Net," Inorganic Chemistry, vol. 44, No. 2, 2005, pp. 181-183.

Shiomi et al., "Molecular Crystals and Liquid Crystals and Technology," Section A (1996), 306, pp. 513-520.

Ferguson et al., Journal of Organometallic Chemistry, 1996, 526(1), pp. 195-198.

Vodak, D.T., et al., Journal of the American Chemical Society, v. 124, 2002, pp. 4942-4943.

Z-Iengtao Xu, Stephen Lee, Yuan-Hon Kiang, Abhijit Basu Mallik, Natia Tsomaia, and Karl T. Mueller, A Cross-linked Large Channel Organic Coordination Solid, Adv. Mater. 2001, 13, No. 9, May 3, pp. 637-641.

Shinji Inagaki, Shiyou Guan, Tetsu Ohsuna and Osamu Terasaki, "An ordered mesoporous organosilica hybrid material with a crystal-like wall structure", Nature, vol. 416, Mar. 21, 2002, pp. 304-307.

Hayal Bulbul Sonmez and Fred Wudl, "Cross-Linked Poly(orthocarbonate)s as Organic Solvent Sorbents", Macromolecules 2005, 38, pp. 1623-1626.

Phillippe Bruent, Eric Demers, Thierry Maris, Gary D. Enright and James D. Wuest, "Designing Permeable Molecular Crystals That React With External Agents to Give Crystalline Products", Angew. Chem. Int. Ed. 2003, 42, pp. 5303-5306.

Vodak, D.T. et al., 'One-Step Synthesis and structure of an Oligo (Spiro-Orthocarbonate), Journal of the American Chemical Society, vol. 124, 2002, pp. 4942-4943. XP002454947.

Supplementary European Search Report of corresponding EP 05 81 6005 dated Oct. 15, 2007.

* cited by examiner

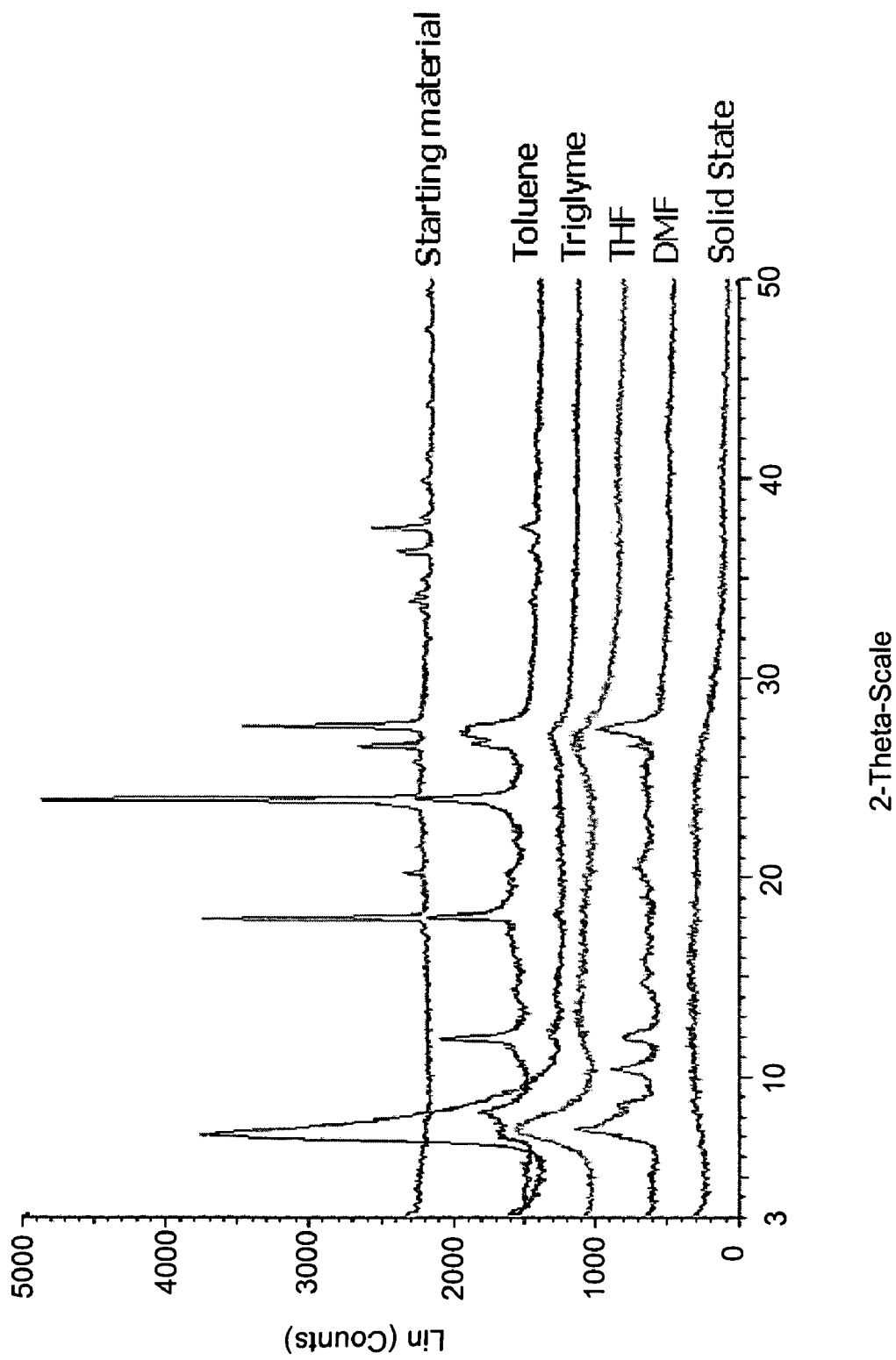
Figure 1. Powder X-ray diffraction patterns of polymerization products.

A.
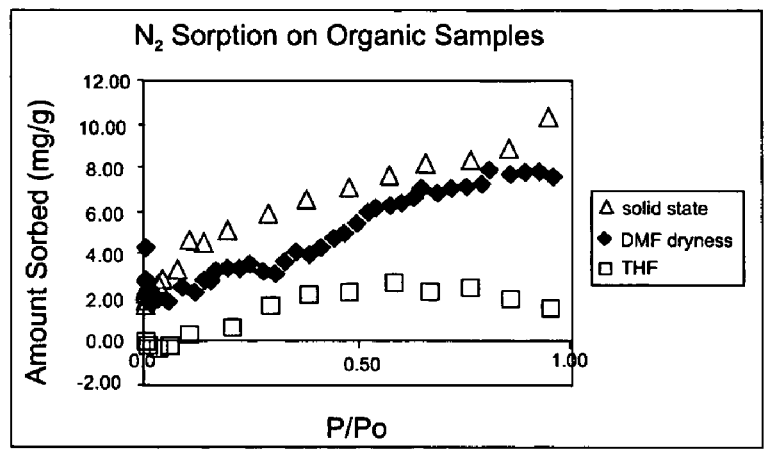
B.
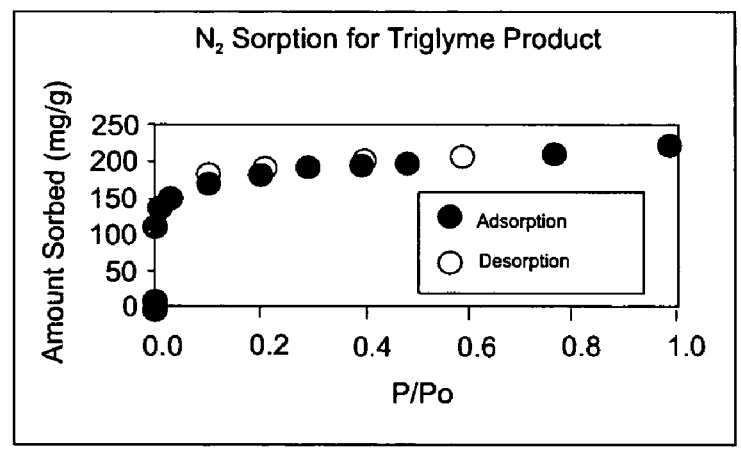
Figure 2. Nitrogen sorption isotherm for (a) nonporous products and (b) the product formed from triglyme solution.

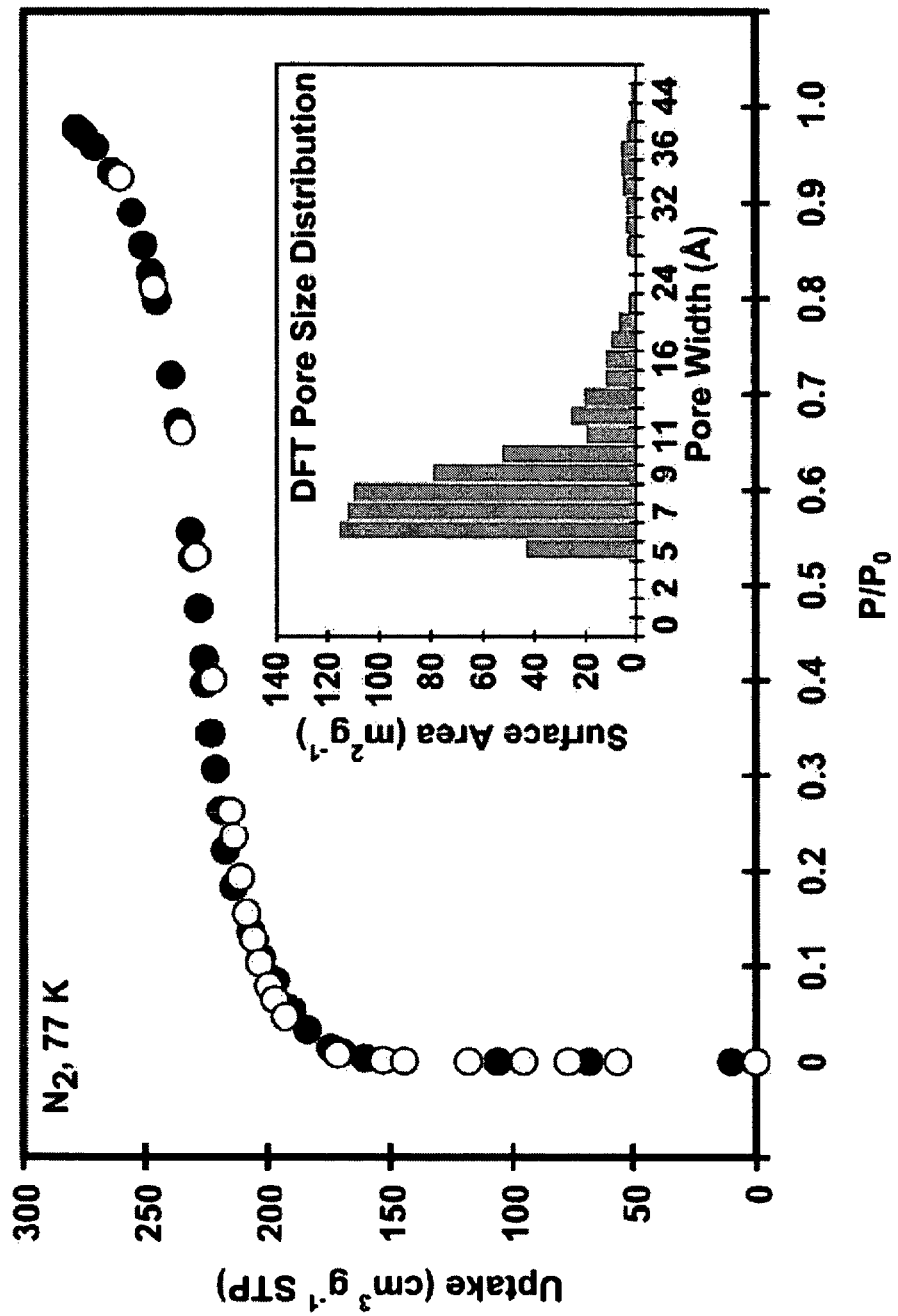
Figure 3. Nitrogen gas adsorption isotherms (main pane) for COF-1 measured at 77 K with pore size histograms (inset panes) calculated after fitting DFT models to adsorption data.

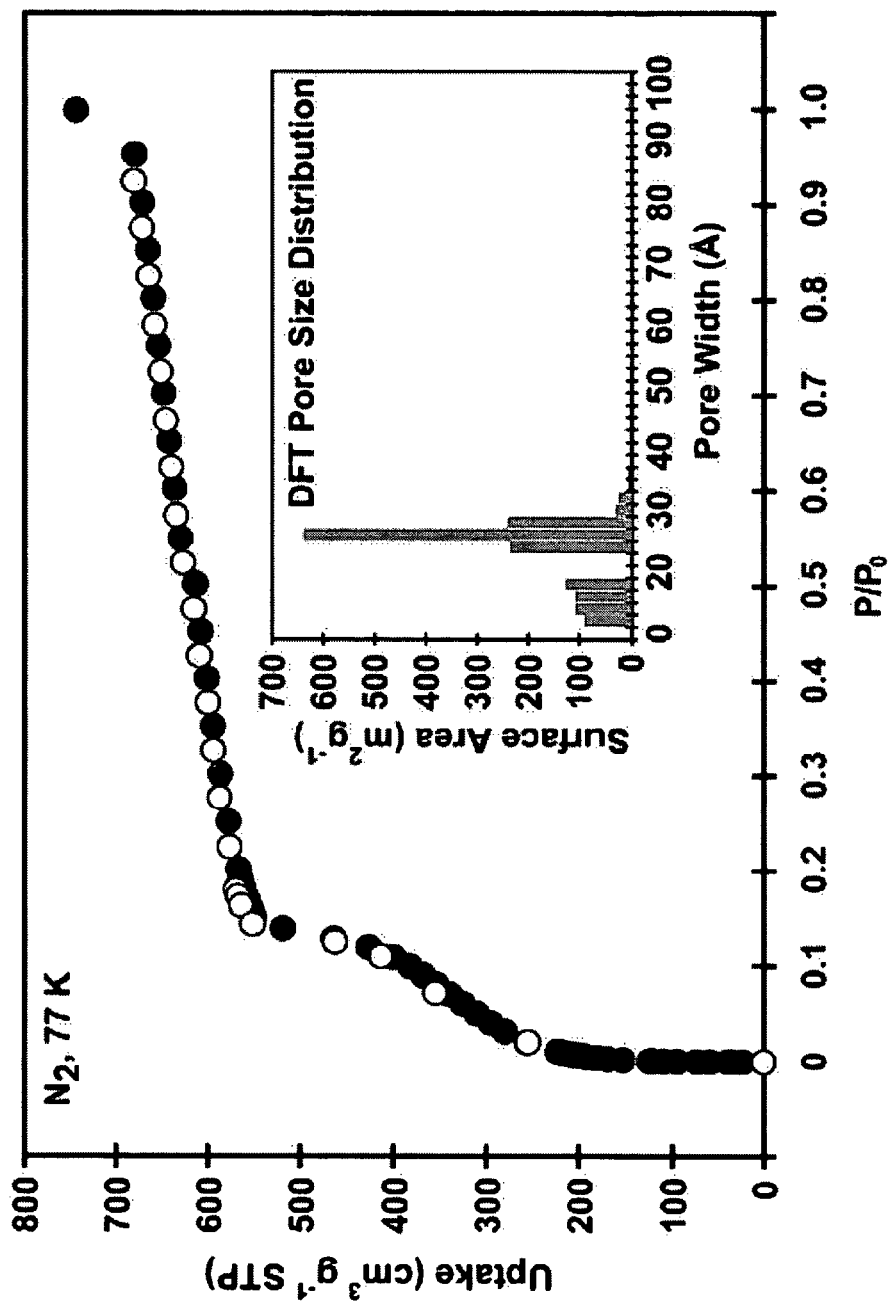
Figure 4. Nitrogen gas adsorption isotherms (main pane) for COF-5 measured at 77 K with pore size histograms (inset panes) calculated after fitting DFT models to adsorption data.

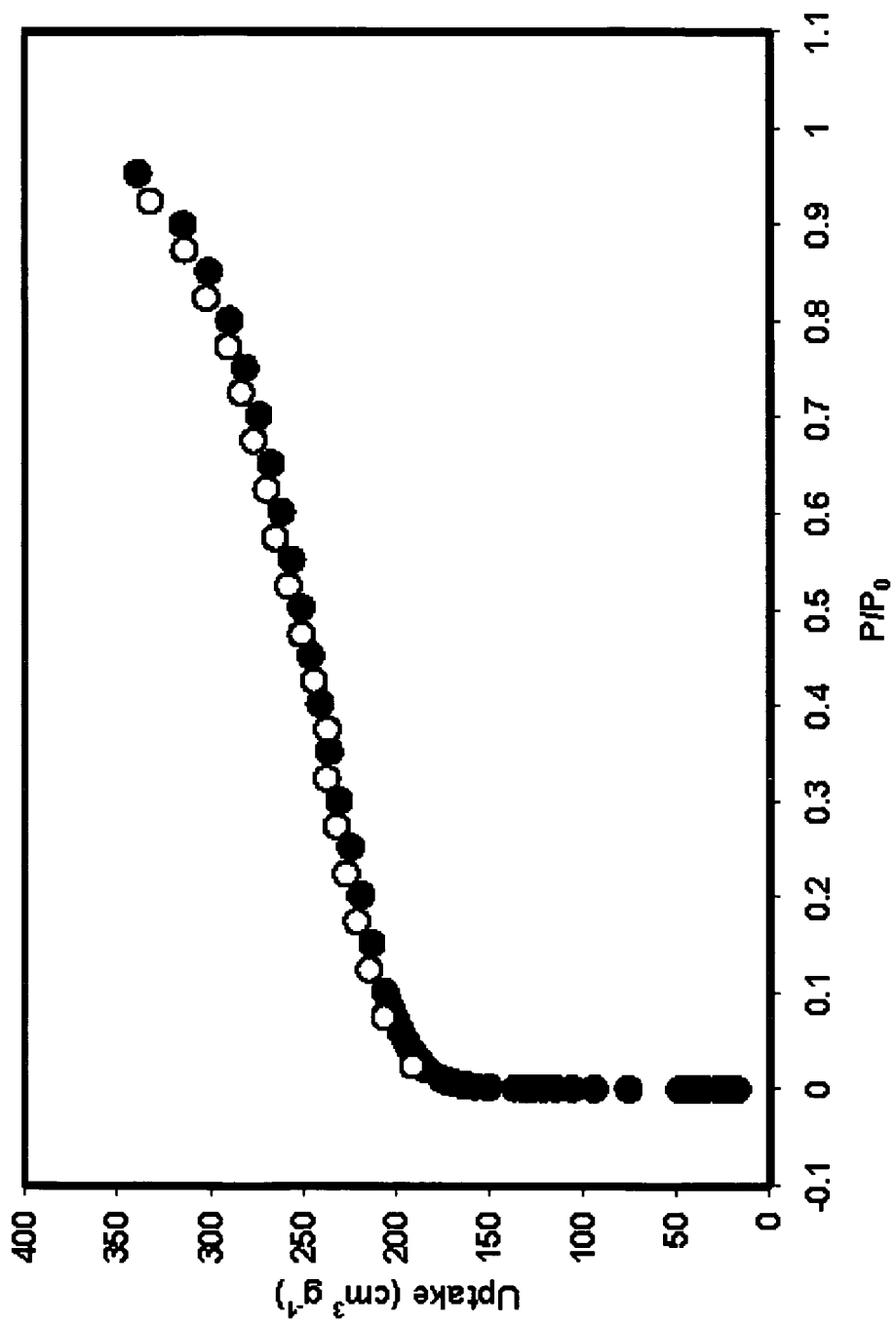
Figure 5. Argon gas isotherm for COF-1 measured at 87 K.

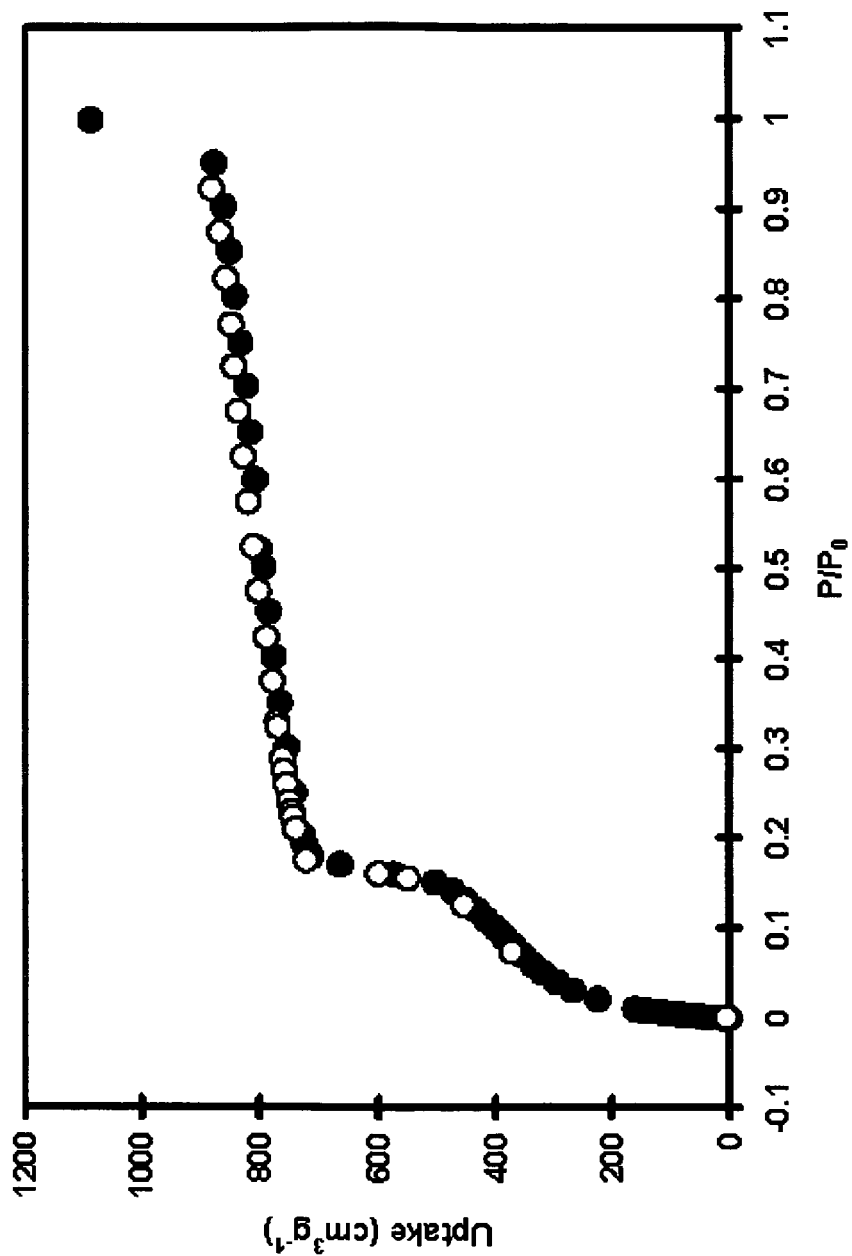
Figure 6. Argon gas isotherm for COF-5 measured at 87 K.

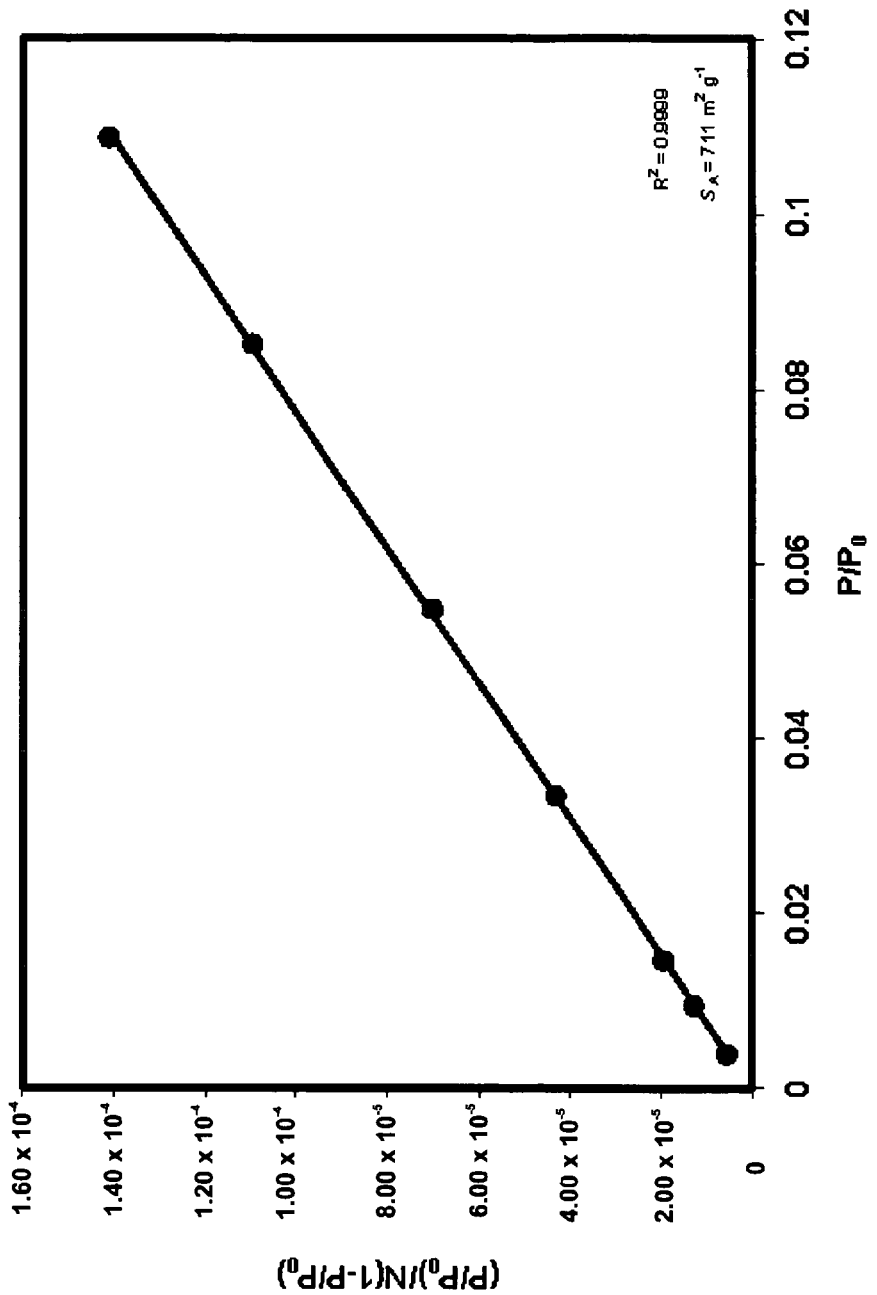
Figure 7. BET plot for COF-1 calculated from nitrogen adsorption data.

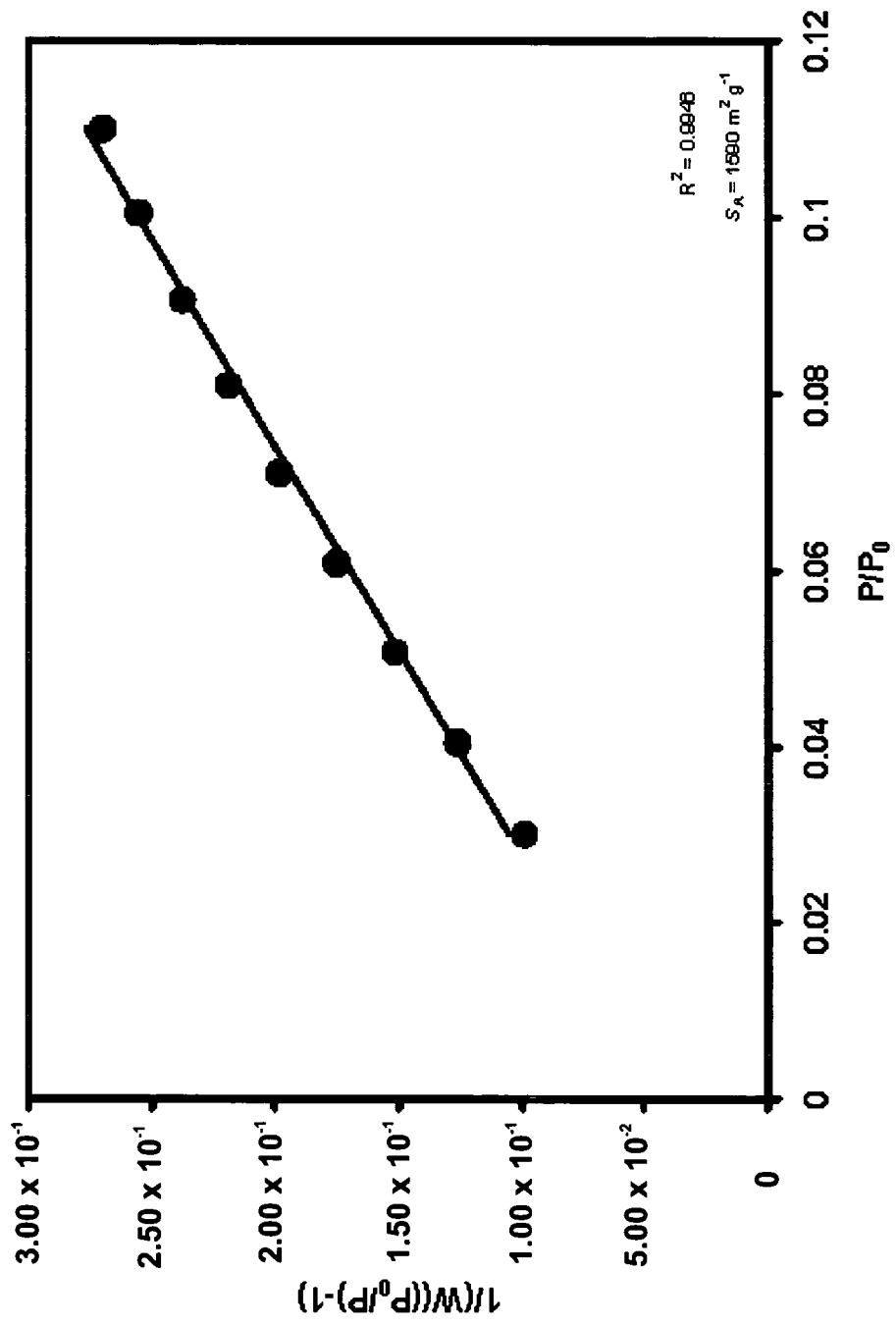
Figure 8. BET plot for COF-5 calculated from nitrogen adsorption data.

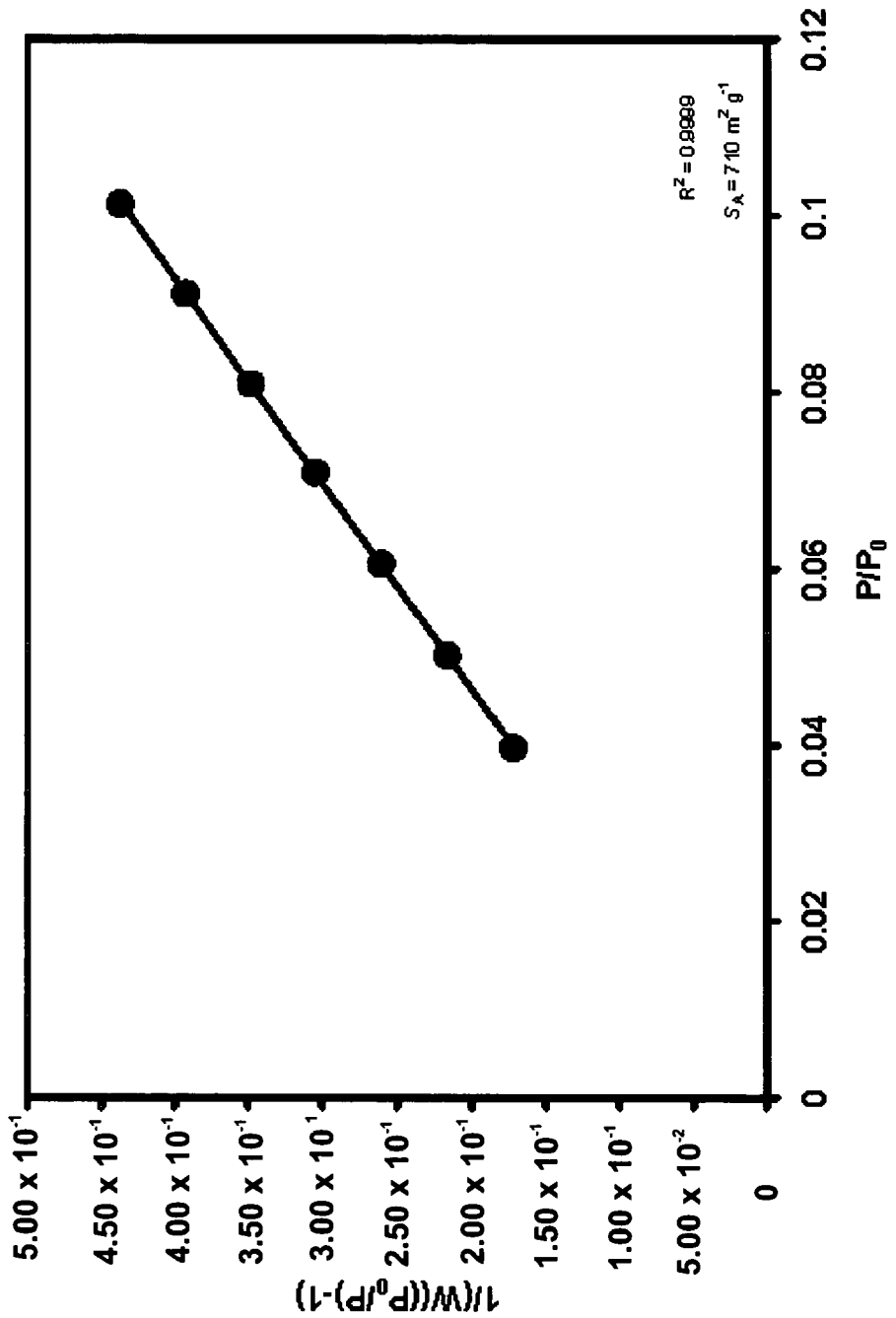
Figure 9. BET plot for COF-1 calculated from argon adsorption data.

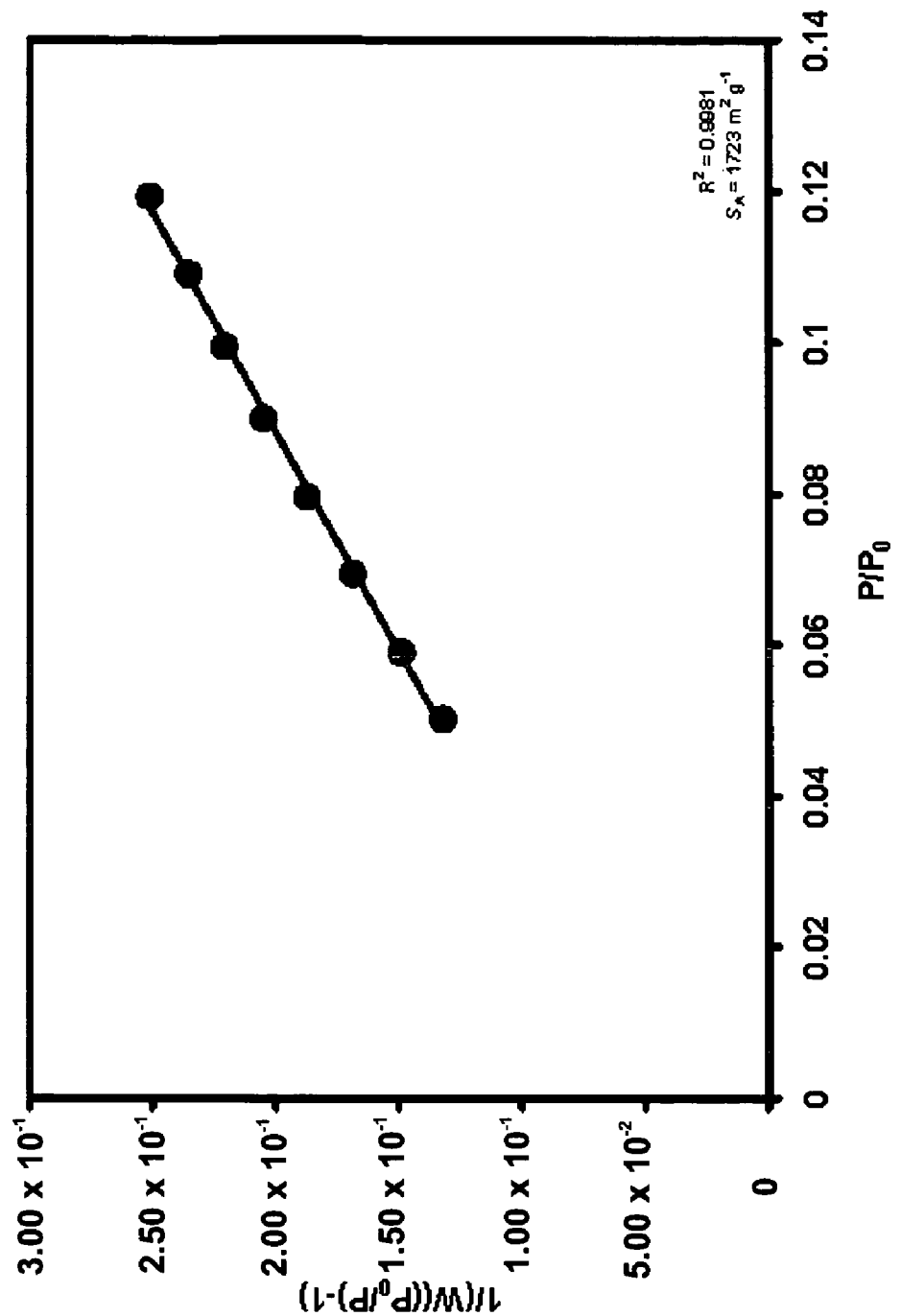
Figure 10. BET plot for COF-5 calculated from argon adsorption data.

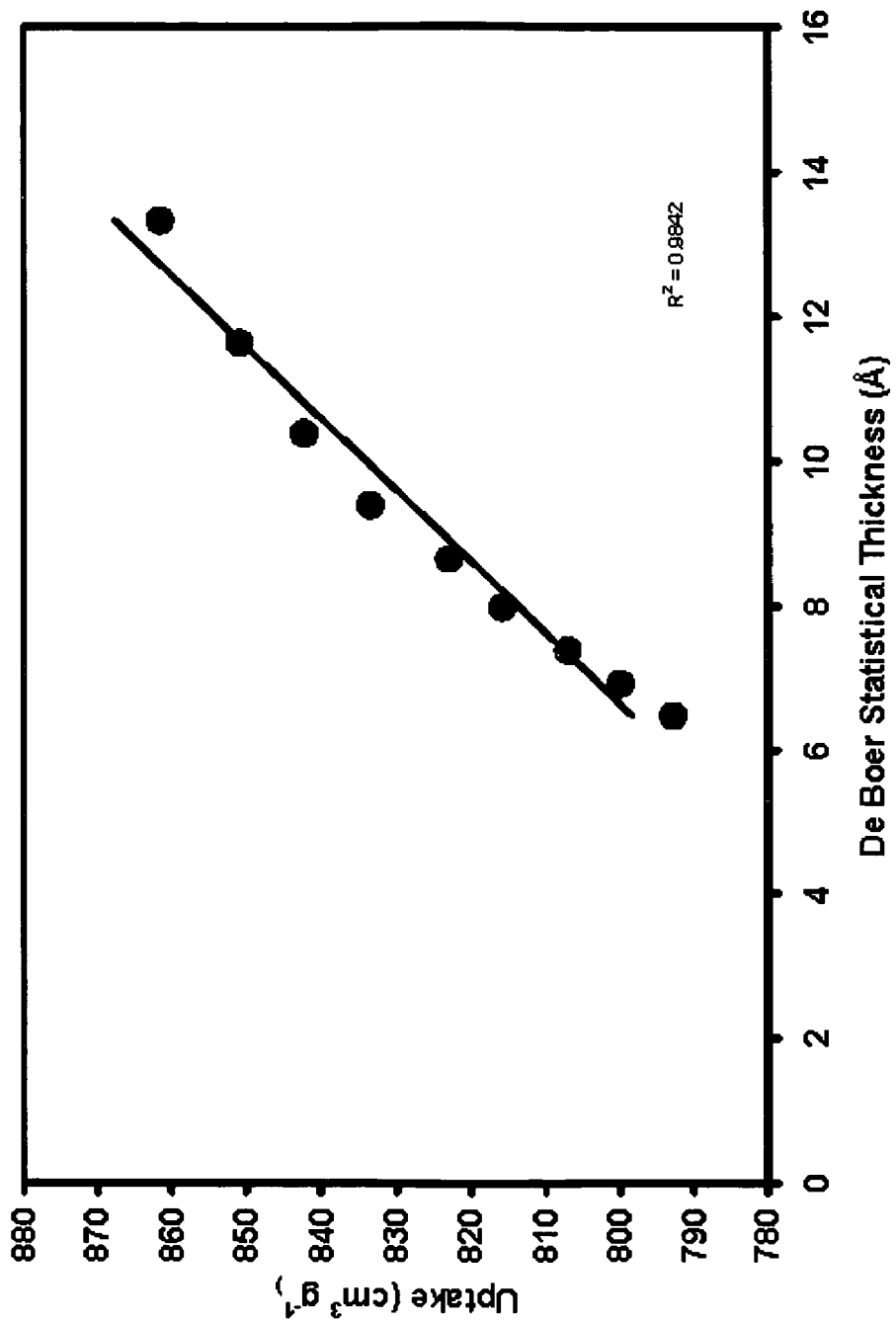
Figure 11. De Boer t-plot for COF-1

COVALENTLY LINKED ORGANIC FRAMEWORKS AND POLYHEDRA

CROSS-REFERENCE TO RELATED APPLICATIONS

This application claims the benefit of U.S. provisional application Ser. No. 60/621,410 filed Oct. 22, 2004.

BACKGROUND OF THE INVENTION

1. Field of the Invention

In at least one aspect, the present invention relates to covalently linked organic networks and methods for forming covalently linked organic networks.

2. Background Art

The formation of covalently linked organic networks has been an elusive goal and an attractive challenge in both molecular design and organic chemistry. These networks can be defined as periodic especially "2-D or 3-D" materials composed of strong, kinetically inert, covalent bonds (e.g. between C, O, N, B). In addition to its stimulating synthetic challenge, properties of these new materials may have important industrial applications taking advantage of their light-weight, inexpensive starting materials, and potentially high chemical and thermal stabilities. By employing specific organic units in a periodic array at the molecular scale, one can specifically tailor structure, functionality, and material properties. For this to be achieved, one needs to operate under mild conditions that do not destroy the structural or physical properties of the building blocks that may be translated into the extended network.

Covalently linked organic networks differ from existing cross-linked polymers and other polymeric materials whose properties are a result of various processing techniques in that organic crystalline networks have clearly defined molecular architectures that are intrinsic to the material. Accurate control over the position of selected organic units in an extended structure is needed to allow optimum exploitation of the material properties.

Existing crystalline covalently linked materials such as diamond, graphite, silicon carbide, carbon nitride, and boron nitride are formed under very high pressures (1-10 GPa) or very high temperatures (500-2400° C.). These extreme synthetic conditions limit the flexibility needed in the formation of extended or functionalized structures, since the structural or chemical integrity of many organic monomer units is not preserved under these conditions.

Current attempts towards synthesizing covalent networks under mild conditions have been unsuccessful in producing extended materials that have periodic molecular structures with long-range order. One such attempt involved the pre-organization of organic moieties via hydrogen bonding or metal-ligand interactions prior to the diffusion of a reactive non-metallic cross-linking agent into the channels. This linked the pre-arranged organic molecules together, and the metal template ions were subsequently removed. Incomplete polymerization or loss of crystallinity upon removal of the metal template ions, however, is often observed.

There has been an increasing demand for porous materials in industrial applications such as gas storage, separations, and catalysis. Some advantages of using completely organic porous materials as opposed to their inorganic or metal-organic counterparts, are that organic materials are lighter in weight, more easily functionalized, and have the potential to be more kinetically stable. In addition, there are environmental advantages to employing extended structures without metal components.

Some current methods of inducing porosity within polymers involve various processing methods or preparation from colloidal systems. All glassy polymers contain some void space (free volume), although this is usually less than 5% of the total volume. It is possible to "freeze-in" up to 20% additional free volume for some glassy polymers with rigid structures by rapid cooling from the molten state below the glass transition temperature, or by rapid solvent removal from a swollen glassy polymer. High free volume polymers are currently used in industrial membranes for transporting either gases or liquids. The voids in these materials, however, are not interconnected and therefore reflect a low accessible surface area as determined by gas adsorption. Moreover, the pore structure is irregular and not homogeneous.

Another existing class of porous organic materials includes polyacetylenes containing bulky substituent groups. The high gas permeabilities of poly(1-trimethylsilyl-1-propyne) ("PT-MSP") have been observed since 1983. This material contained a large free volume (~30%), and was able to separate organic compounds from gases or water. The stability of PTMSP is limited by its rapid loss of microporosity from reaction by heat, oxygen, radiation, UV light, non-uniform pore structure, or any combination of the above.

One recent display of porous organic materials is the polymers of intrinsic microporosity (PIMs). These polymers have been reported to contain relatively high surface areas (430-850 $m^2/g$) measured by gas adsorption due to their highly rigid and contorted molecular structures unable to efficiently pack in space. These materials, however, display marked hysteresis at low pressures.

Thermal dehydration of phenyl boronic acids has been known to form six-member boronic acid anhydride (boroxine) rings. Although crystal structures of molecular compounds containing one boroxine ring have been studied, little if anything is known about materials produced from the condensation of multi-topic boronic acids.

SUMMARY OF THE INVENTION

The present invention solves one or more problems of the prior art by providing in at least one embodiment a covalently linked organic network comprising a plurality of boron-containing clusters linked together by a plurality of linking groups. If the present invention is further characterized by having each linking group bonded to at least two distinct boron-containing clusters. The covalently linked organic networks of the invention are particularly useful lightweight, crystalline, or semi-crystalline bulk products for gas storage applications.

BRIEF DESCRIPTION OF THE DRAWINGS

FIG. 1 provides Powder X-ray Diffraction ("PXRD") patterns of polymerization products from the monomer described by formula XVII;

FIG. 2 provides a nitrogen sorption isotherm for (a) non-porous polymerization products and (b) the product formed from triglyme solution each derived from the monomer described by formula XVII;

FIG. 3 provides a nitrogen gas adsorption isotherm (main pane) for COF-1 measured at 77 K with pore size histogram (inset pane) calculated after fitting DFT models to adsorption data;

FIG. 4 provides a nitrogen gas adsorption isotherm (main pane) for COF-5 measured at 77 K with pore size histogram (inset pane) calculated after fitting DFT models to adsorption data;

FIG. 5 provides an argon gas isotherm for COF-1 measured at 87 K;

FIG. 6 provides an argon gas isotherm for COF-5 measured at 87 K;

FIG. 7 provides BET plot for COF-1 calculated from nitrogen adsorption data;

FIG. 8 provides BET plot for COF-5 calculated from nitrogen adsorption data;

FIG. 9 provides a BET plot for COF-1 calculated from argon adsorption data;

FIG. 10 provides a BET plot for COF-5 calculated from argon adsorption data; and FIG. 11 provides a De Boer t-plot for COF-1.

DETAILED DESCRIPTION OF THE PREFERRED EMBODIMENT(S)

Reference will now be made in detail to presently preferred compositions or embodiments and methods of the invention, which constitute the best modes of practicing the invention presently known to the inventors.

The term "cluster" refers to identifiable associations of 2 or more atoms. Such associations are typically established by some type of bond—ionic, covalent, Van der Waal, and the like.

The term "covalent organic network" refers collectively to both covalent organic frameworks and to covalent organic polyhedra.

The term "covalent organic polyhedra" refers to a non-extended covalent organic networks. Polymerization in such polyhedra does not occur usually because of the presence of capping ligands that inhibit polymerization.

The term "covalent organic framework" refers to an extended covalent organic network having clusters connected by linking groups. These structures are extended in the same sense that polymers are extended.

As used herein, a line in a chemical formula with an atom on one end and nothing on the other end means that the formula refers to a chemical fragment that is bonded to another entity on the end without an atom attached. Sometimes for emphasis, a wavy line will intersect the line.

In an embodiment of the present invention, a covalently linked organic network is provided. The covalently linked organic network of the invention comprises a plurality of boron-containing clusters linked together by a plurality of organic linking groups. Variations of the covalently linked organic networks (both the frameworks and polyhedra) have surface areas from about 1 to about 20,000 m²/g. Other variations have surface areas from about 1,000 to about 10,000 m²/g. The present invention is further characterized by having each linking group bonded to at least two distinct boron-containing clusters. In a variation of the present embodiment, the covalently linked organic networks are covalently linked organic frameworks ("COFs") which are extended structures. In a further refinement these COFs are crystalline materials that may be either polycrystalline or even single crystals. Because of the extended nature of the covalently linked organic frameworks of the invention, the plurality of boron-containing clusters comprises at least 10 boron-containing clusters. In other variations of the invention, the plurality of boron-containing clusters comprises at least 100 boron-containing clusters. Similarly, because of the extended nature of the covalently linked organic frameworks, the plurality of linking groups comprises at least 10 linking groups. In other variations, the plurality of linking groups comprises at least 100 linking groups. Since the covalently bonded organic frameworks are extended structures, variation may form into analogous nets to the nets found in metallic organic frameworks as described in Reticular Chemistry: Occurrence and Taxonomy of Nets and Grammar for the Design of Frameworks, Acc. Chem. Res. 2005, 38, 176-182. The entire disclosure of this article is hereby incorporated by reference.

In addition to the COFs, the covalent organic networks of the present invention also include covalent organic polyhedra. Covalent organic polyhedra are covalent organic networks that comprise a plurality of boron-containing clusters linked together by a plurality of organic linking groups such that the spatial structure of the network is a polyhedron. Typically, the polyhedra of this variation are 2 or 3 dimensional structures.

In an important variation of the invention, the boron-containing clusters include a structure described by the formula $B_xQ_yC_z$ wherein Q is oxygen, sulfur, nitrogen, or phosphorus; x and y are integers such that the valency of B is satisfied, and z is an integer from 0 to 6. In a particularly useful variation, the boron-containing cluster has the formula $B_xO_y$ An example of such a boron-containing cluster is described by Formulae I and II:

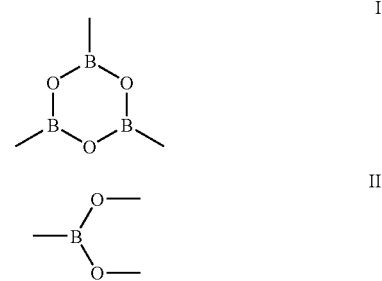

The boron-containing cluster of Formula I is able to be bonded to 3 different linking groups while the cluster of Formula II is most advantageously bonded to 2 different linking groups with the two oxygen atoms bonded to a single linking group that is bidentate at least on one end. In another variation of the invention, the boron-containing cluster is described by Formulae III-IV:

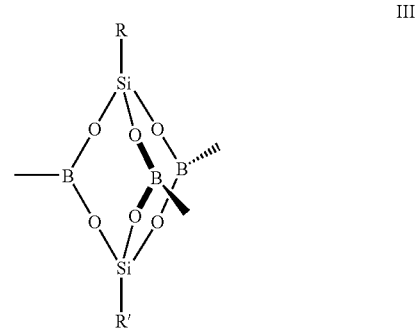

-continued

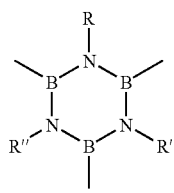
IV wherein R, R', and R" are each independently hydrogen, alkyl, aryl, halogen, and the like. In the case of Formula III, t-butyl is particularly useful.

As set forth above, the plurality of boron-containing clusters are linked together by a plurality of linking groups to form an extended framework or a polyhedron. Suitable linking groups include one or more components selected from the group consisting of substituted or unsubstituted aromatic rings, substituted or unsubstituted heteroaromatic rings, substituted or unsubstituted nonaromatic rings, substituted or unsubstituted nonaromatic heterocyclic rings, or saturated or unsaturated, substituted or unsubstituted, hydrocarbon groups. The saturated or unsaturated hydrocarbon groups may include one or more heteroatoms. In a variation of the invention, the linking group is described by Formula V:

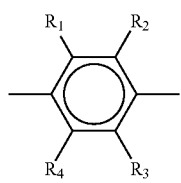
V wherein $R_1$, $R_2$, $R_3$, and $R_4$ are each independently H, alkyl, aryl, OH, alkoxy, sulfur-containing groups (e.g., thioalkoxy), silicon-containing groups, halogen, nitro, amino, cyano, boron-containing groups, phosphorus-containing groups, carboxylic acids, or esters.

In another variation of the invention, the linking group is described by Formula VI:

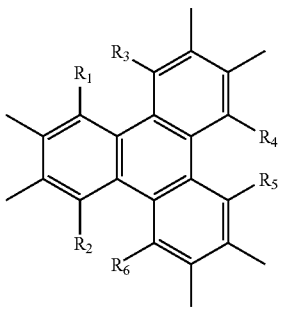
VI wherein $R_1$, $R_2$, $R_3$, $R_4$, $R_5$, and $R_6$ are each independently H, alkyl, aryl, OH, alkoxy, sulfur-containing groups (e.g., thioalkoxy), silicon-containing groups, halogen, nitro, amino, cyano, boron-containing groups, phosphorus-containing groups, carboxylic acids, or esters.

In another variation of the invention, the linking group is described by Formulae VII-X:

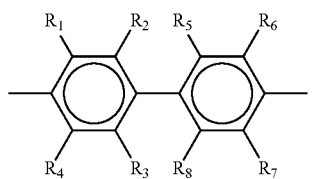
VII

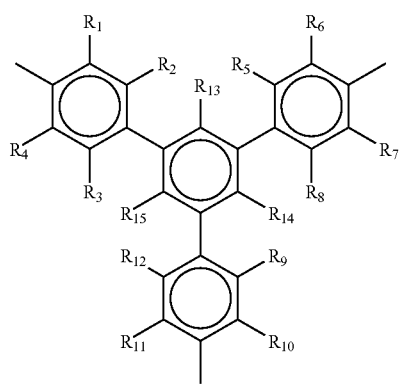
VIII

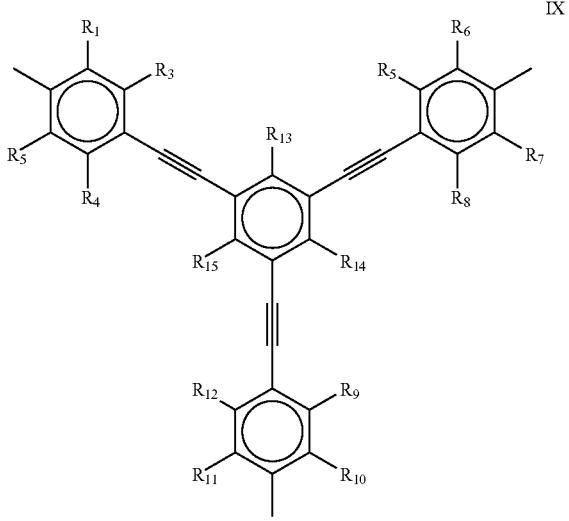
IX

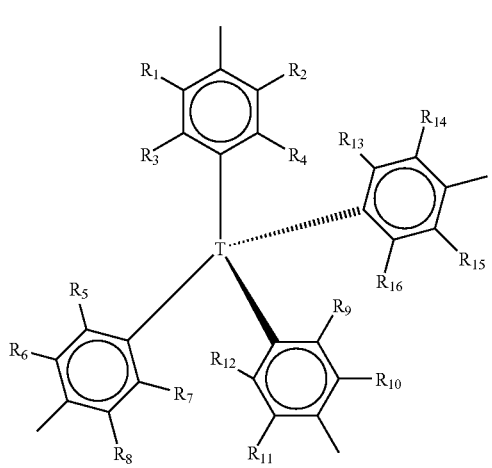

X wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ are each independently H, alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters and T is a tetrahedral atom (e.g., carbon, silicon, germanium, tin) or a tetrahedral group or cluster.

In another variation of the invention, the linking group is described by Formula XI:

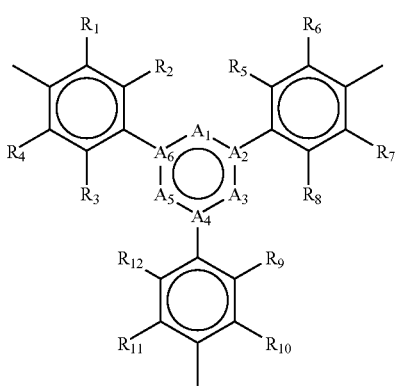

XI wherein $A_1$, $A_2$, $A_3$, $A_4$, $A_5$, and $A_6$ are each independently absent or any atom or group capable of forming a sable ring structure and $R_1$, $R_2$, $R_3$, $R_4$, $R_5$, $R_6$, $R_7$, $R_8$, $R_9$, $R_{10}$, $R_{11}$, and $R_{12}$ are each independently H, alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters. Specific examples of Formula VIII are provided by Formulae XII and XIII and ammonium salts of the linking groups of Formulae XII and XIII:

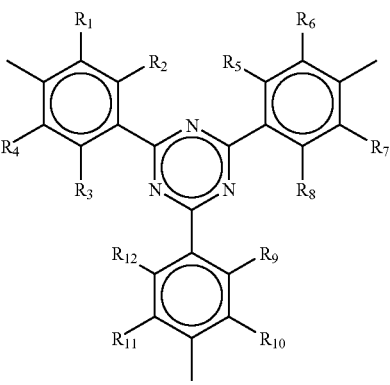

XII

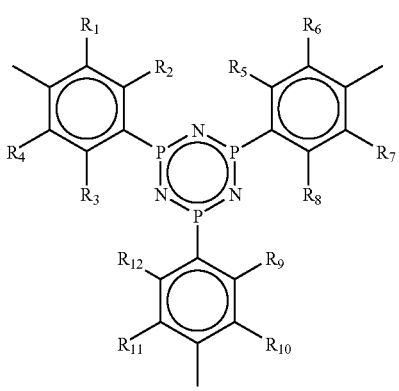

XIII wherein $R_1$, $R_2$, $R_3$, $R_4$, $R_5$, $R_6$, $R_7$, $R_8$, $R_9$, $R_{10}$, $R_{11}$, and $R_{12}$ are each independently H, alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

In yet another variation of the invention, the linking group is described by Formula XIV:

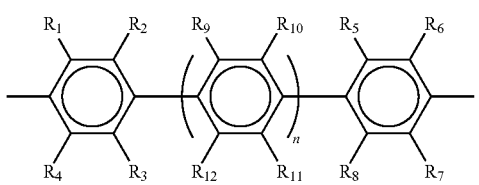

XIV wherein $R_1$ through $R_{12}$ are each independently H, alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters; and n is an integer greater than or equal to 1.

In still another embodiment of the invention, a portion of the plurality of linking groups comprise a linking group which forms a first bond with a first boron-containing cluster and a second bond with a second boron-containing cluster such that the angle between the first bond and the second bond is less than 180 degrees. Examples of such linking groups include linking groups described by Formula XV:

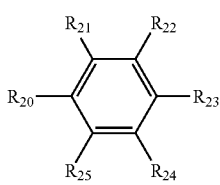

XV wherein $R_{20}$, $R_{21}$, $R_{22}$, $R_{23}$, $R_{24}$, and $R_{25}$ are each independently H, alkyl, OH, alkoxy, sulfur-containing groups (e.g., thioalkoxy), silicon-containing groups, halogen, nitro, amino, cyano, boron-containing groups, phosphorus-containing groups, carboxylic acids, esters, or a bond to a member of the plurality boron containing cluster. This variation is further characterized with the proviso that at least two groups of $R_{20}$-$R_{25}$ are bonds to two distinct members of the plurality of boron containing clusters such that the angle between these bonds are less than 180°.

Another example of such linking groups are described by Formula XVI:

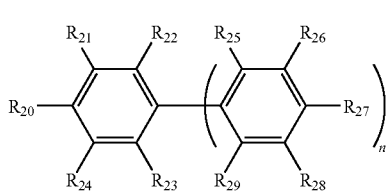

XVI wherein $R_{20}$ through $R_{29}$ are each independently H, alkyl, OH, alkoxy, sulfur-containing groups (e.g., thioalkoxy), silicon-containing groups, halogen, nitro, amino, cyano, boron-containing groups, phosphorus-containing groups, carboxylic acids, esters, or a bond to a member from the plurality boron-containing cluster. This variation is further characterized with the proviso that at least two groups of $R_{20}$-$R_{29}$ are bonds to two distinct members of the plurality of boron containing clusters such that the angle between these bonds are less than 180°.

The covalently linked organic frameworks or polyhedra of the invention optionally further comprise a guest species. Such a guest species may increase the surface area of the covalently linked organic networks. In a similar manner, the covalently linked organic networks of the invention further comprises an adsorbed chemical species. Such adsorbed chemical species include for example, ammonia, carbon dioxide, carbon monoxide, hydrogen, amines, methane, oxygen, argon, nitrogen, organic dyes, polycyclic organic molecules, metal ions, inorganic clusters, organometallic clusters, and combinations thereof.

In another embodiment of the invention, a method for forming the covalently linked organic frameworks and polyhedra set forth above is provided. In one variation of this embodiment, the method of the invention utilizes a monomer condenses into extended crystalline materials be selected. Such monomers typically have one or more boronic acid groups allowing self-condensation of the monomer. The crystalline product may be either polycrystalline or single crystal. In one example of this variation, the reversibility of boroxine ring formation and cleavage makes this system attractive for single crystal formation. In general, the monomer will be a multitopic boronic acid or boronic ester derivative. For example, the condensation of multi-topic boronic acid and boronic ester derivatives form porous, semicrystalline to crystalline organic materials with high surface areas. In another variation of this embodiment, aromatic polyalcohols and compounds having one or more boronic acid groups (polyboronic acids) are reacted together to form either the covalent organic frameworks or polyhedra of the invention.

In accordance with the methods of the invention, phenylene bisboronic acids are condensed to form microporous crystalline compounds with high surface. It has been reported in the structure of triphenylboroxine that the central $B_3O_3$ rings are found to be nearly planar, and the phenyl groups are nearly coplanar with boroxine ring (Scheme 1).

Scheme 1

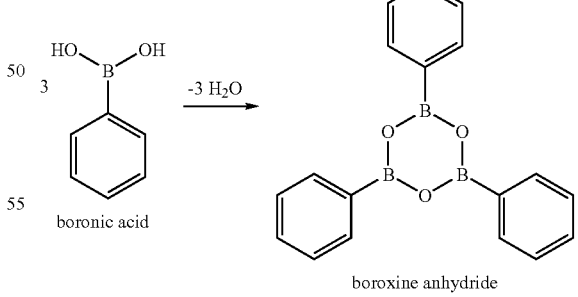

In one variation of the method of the invention, the prior art is extended by dehydration of the compound described by Formula XVII to form COF-1 as depicted in Scheme 2.

Scheme 2
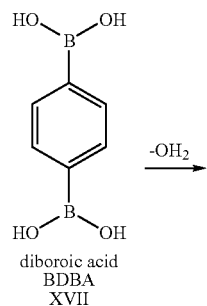
diboroic acid
BDBA
XVII
−OH₂ →
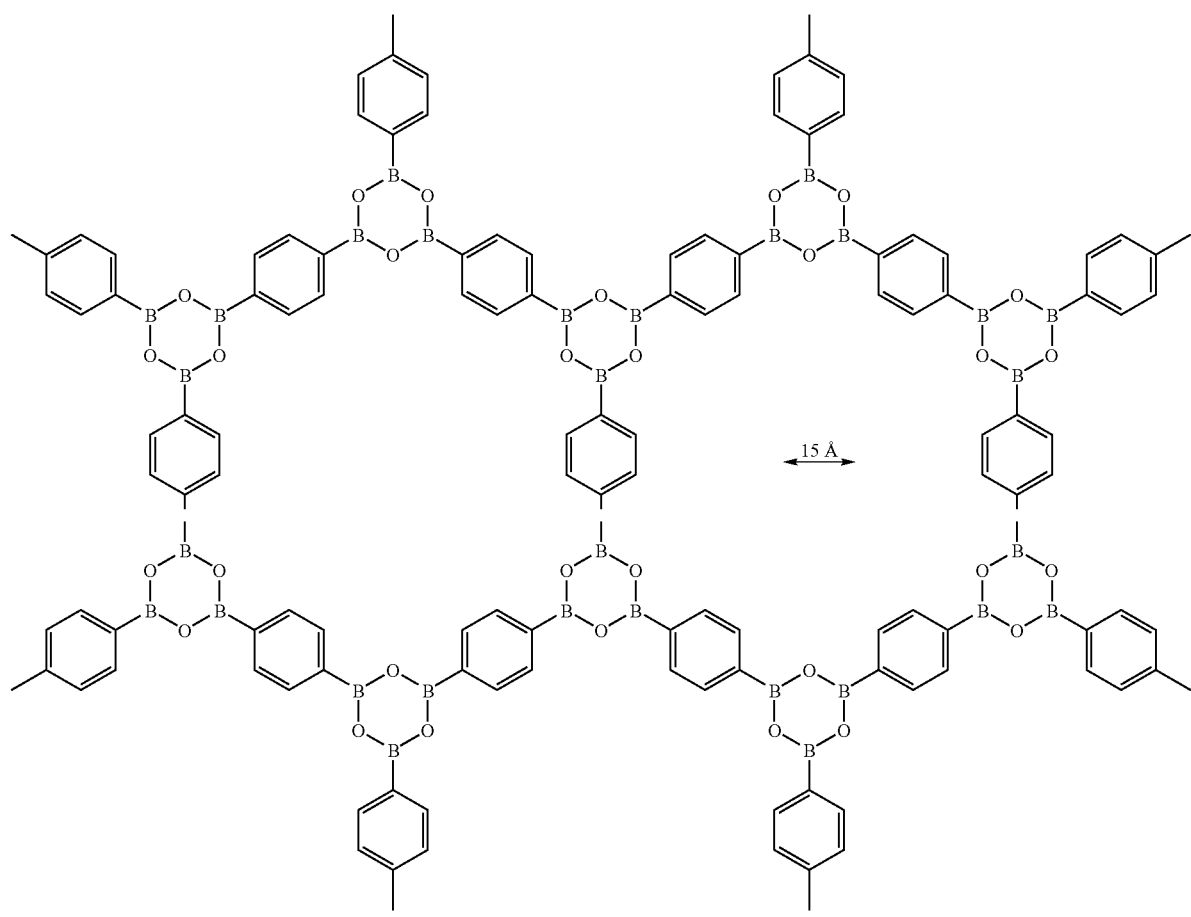
COF-1

The aromatic rings of both the starting materials and products of Scheme 1 are optionally substituted with alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

The reactions of schemes 1 and 2 are extended by Schemes 3 and 4. In accordance with Scheme 3, the dehydration reaction between phenylboronic acid and 2,3,6,7,10,11-hexahydroxytriphenylene ("HHTP"), a trigonal building block, gives a new 5-membered $BO_2C_2$ ring.

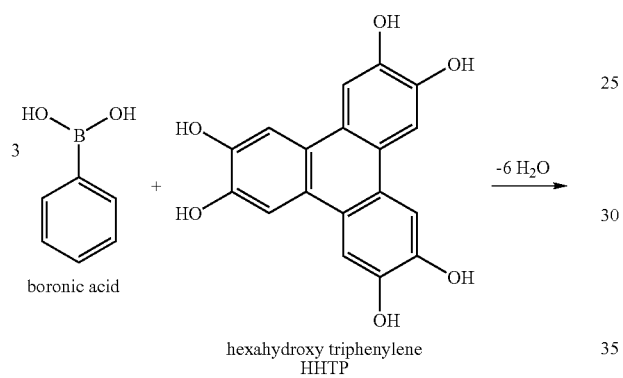

Scheme 3

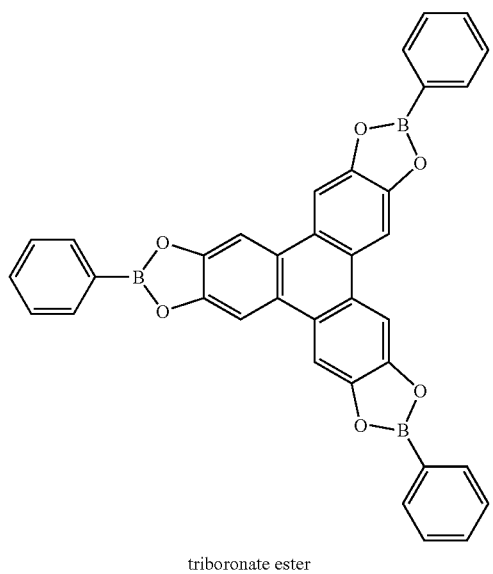

triboronate ester

Scheme 4 provides a reaction for a substantially co-planar extended sheet structure ("COF-5").

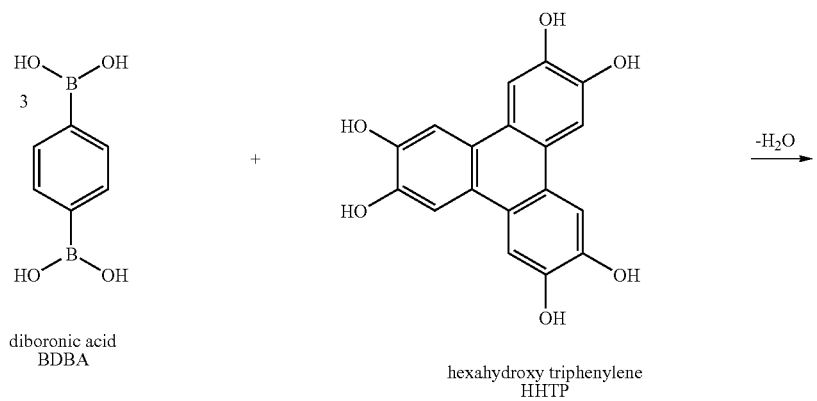

Scheme 4

-continued
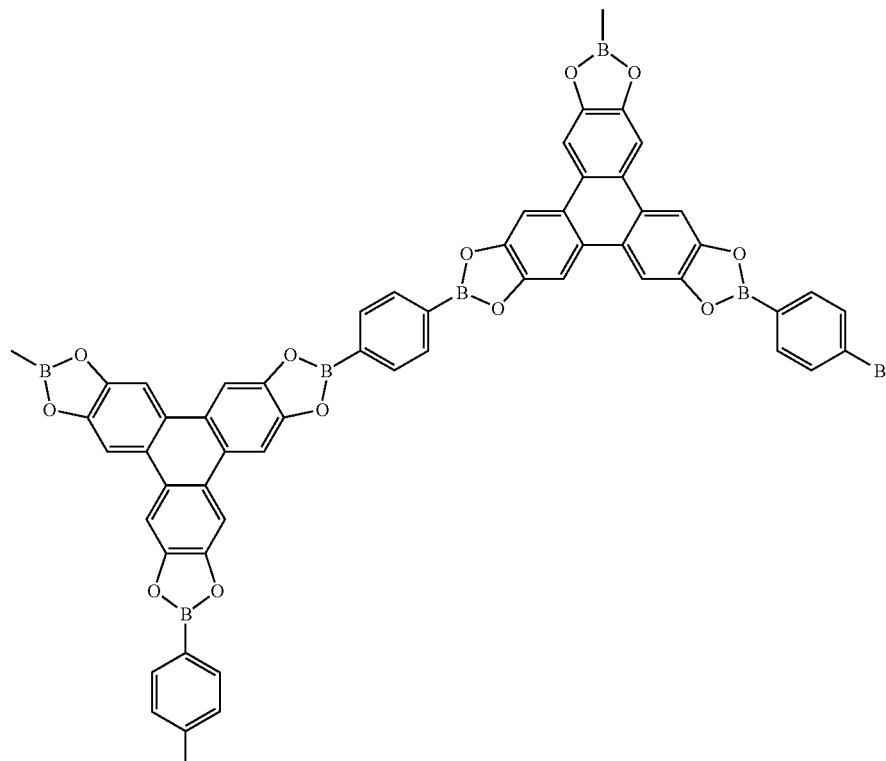
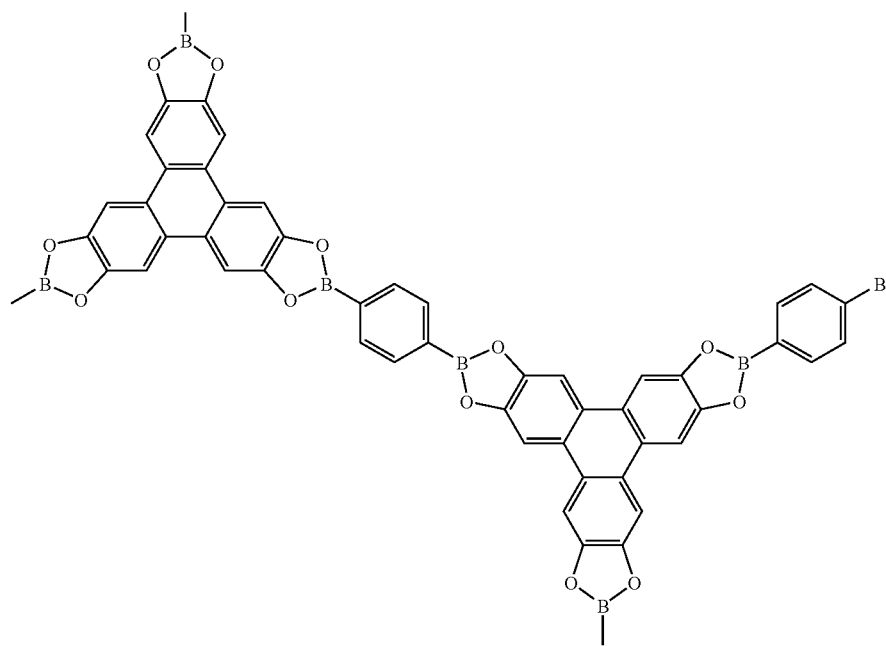

-continued

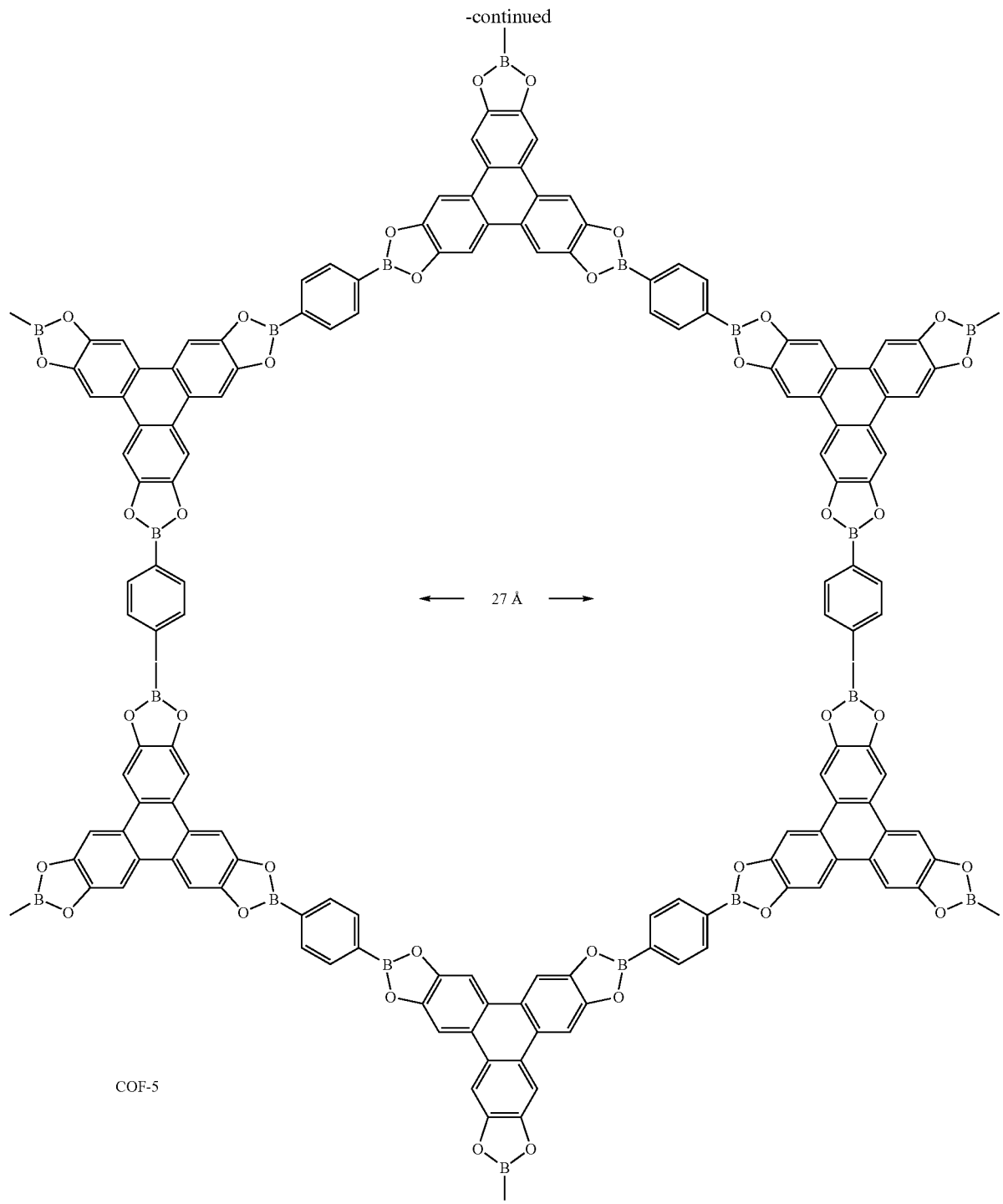

COF-5

The aromatic rings of both the starting materials and products of Scheme 4 are optionally substituted with alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

The direct condensation of boronic acids with tert-butylsilanetriol ("TBST") in aromatic solvents with azeotropic removal of $H_2O$ is known to form borosilicate cage compounds, specifically a Si capped trigonal biprismatic cluster which can be regarded as a trigonal planar SBU. TBST is accepted as being the best reagent for this co-condensation chemistry because the bulky tert-butyl group of TBST kinetically inhibits its self-condensation to form dense and amorphous polysilsequioxanes. Additionally, reaction of organotrichlorosilanes (i.e. $RSiCl_3$) with boronic acids is another route to access borosilicate COFs where HCl will be the by-product rather than $H_2O$. This strategy may be more advantageous since acids/bases can easily be added to control reaction rates facilitating nucleation of crystalline COF phases. Scheme 5 provides the equation for a reaction known to produce discrete organoborosilicate clusters Scheme 5

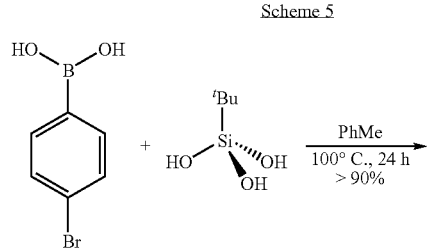

Extension of the reaction methodology in Scheme 5 to co-condensation with polytopic boronic acids provides a novel strategy to produce 3-connected COFs like those described above via formation of boroxine rings. From structural data from the discrete borosilicate compound illustrated above, the phenyl rings adopt a co-planar conformation with the BO$_2$ plane via the aforementioned intramolecular hydrogen bonding. So, again, the rationalization provided above for the topology of expected COF structures described above is extended here for borosilicate COFs. Initial work points to improved stability toward hydrolysis compared to boroxine and boronate ester COFs, a property perhaps imparted by the steric protection of the greasy tert-butyl group that shrouds the SBU. Reactions in aromatic solvents (e.g. toluene), like those used for discrete compounds, represents a logical starting point for COF synthesis. Scheme 6 provides an example of the reaction of BDBA with TBST to form a 3-connected sheet.

Scheme 6

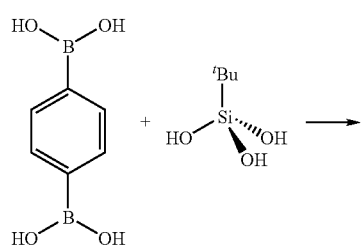

-continued

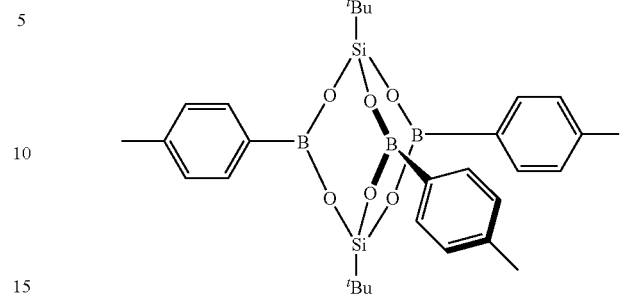

In an analogous manner as set forth above, the aromatic rings of both the starting materials and products of Scheme 6 are optionally substituted with alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

With reference to Scheme 7, self-condensation of tetrakis[phenyl-4-boryl(dihydroxy)]methane (TPBM) leads to isolation of 4,3 connected COFs (designated as "COF-10") via boroxine ring formation. The aromatic rings of the TPBM of Scheme 7 (along with the corresponding rings on the product) are optionally substituted with alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

Scheme 7

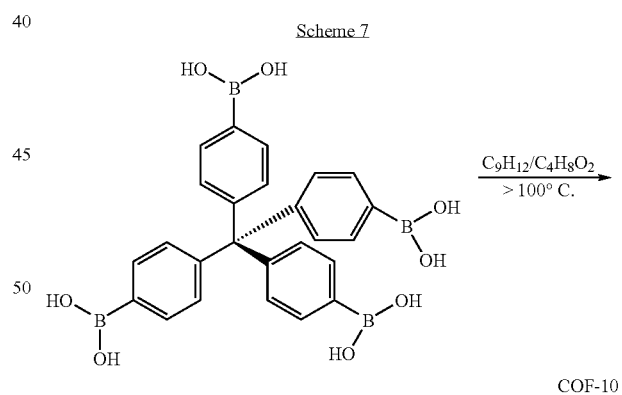

COF-10

With reference to Scheme 8, the co-condensation of TPBM with 1,2,4,5-tetrahydroxybenzene (THB) to form an expanded diamond structure is illustrated. In this reaction THB functions as a linear link lying co-planar with the phenyl rings of TPBM in the COF product. Again, each of the aromatic rings in the TPBM and THB are optionally substituted with alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

Scheme 8
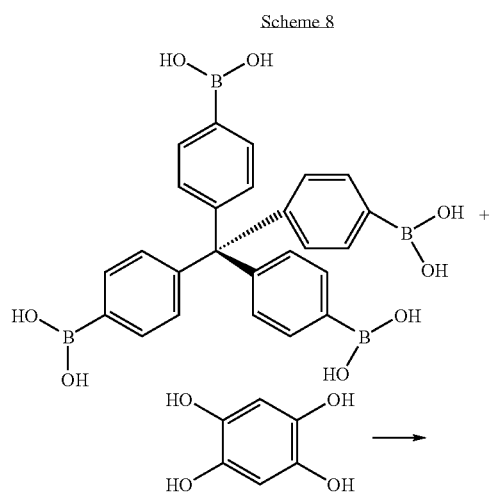
Similarly, with reference to Scheme 9 reaction of hexahydroxytriphenylene ("HHTP") with TPBM provides a route to synthesize a COF designated as COF-11:
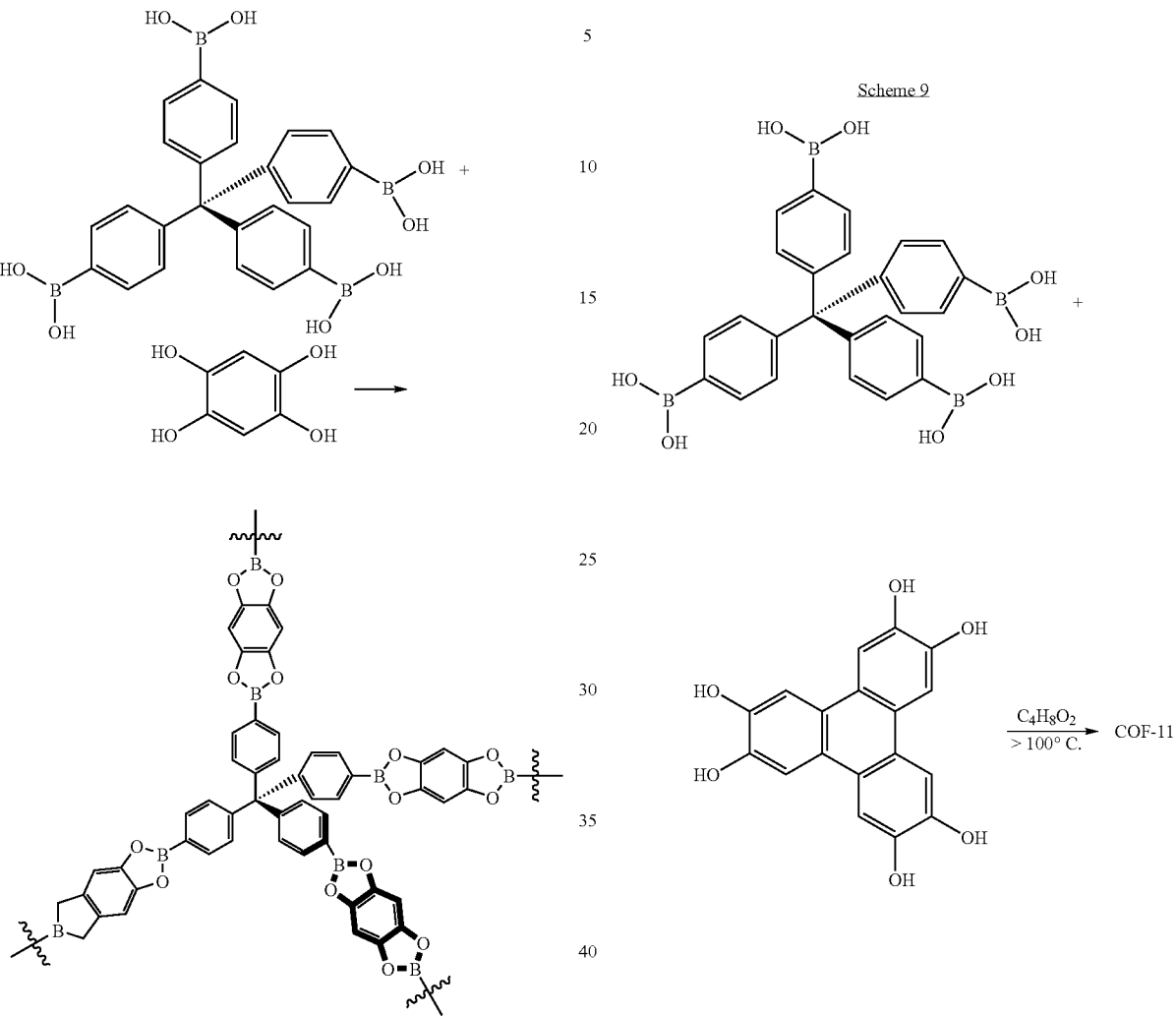
COF-11 includes moieties having formula XX.
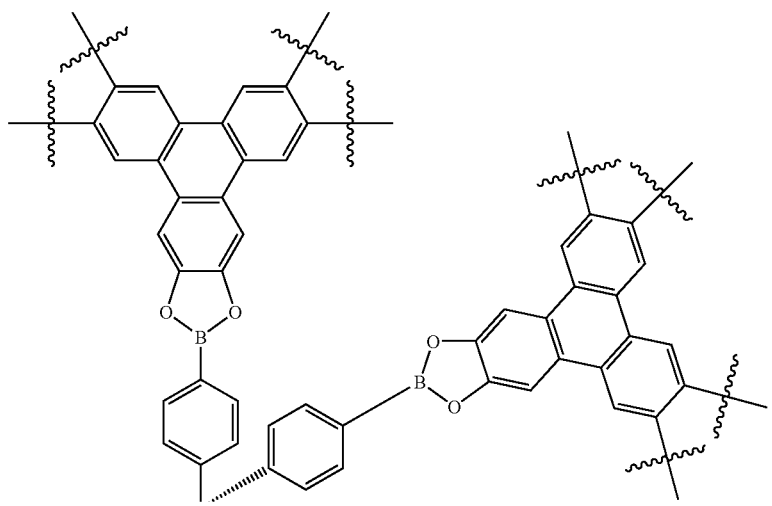
XX

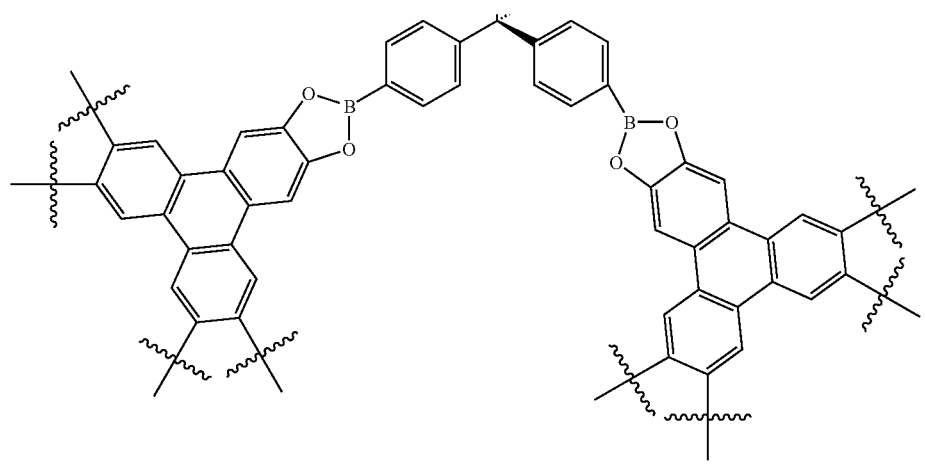

With reference to Scheme 10, the formation of 1D crystalline polymers from reaction of BDBA with pentaerythritol is provided. The products of this reaction are exceptionally stable, and are in fact best synthesized in water. It is believed that the presence of a stable 6-membered ring in the product imparts this stability. Moreover, pentaerythritol does not serve as a linear link, i.e., it will connect boronic acid groups at a −145°. Scheme 10 provides the co-condensation of Pentaerythritol with BDBA.

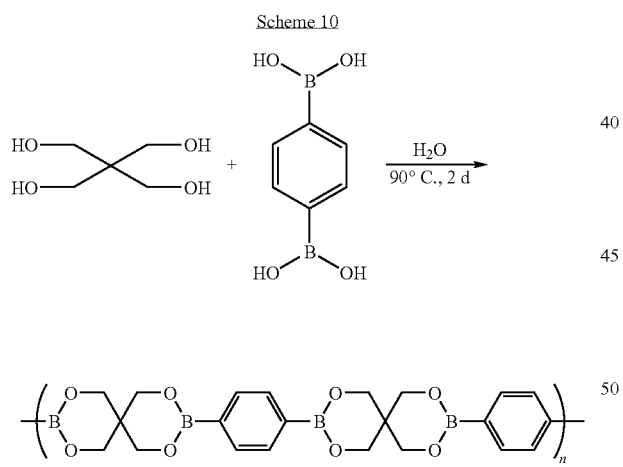

Similarly, Scheme 11 illustrates the co-condensation of TPBM with pentaeryhtritol to produce a covalently linked organic network designated COF-12. COF-12 includes moieties having formula XXI. Again, each of the aromatic rings in Schemes 10 and 11 are optionally substituted with alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

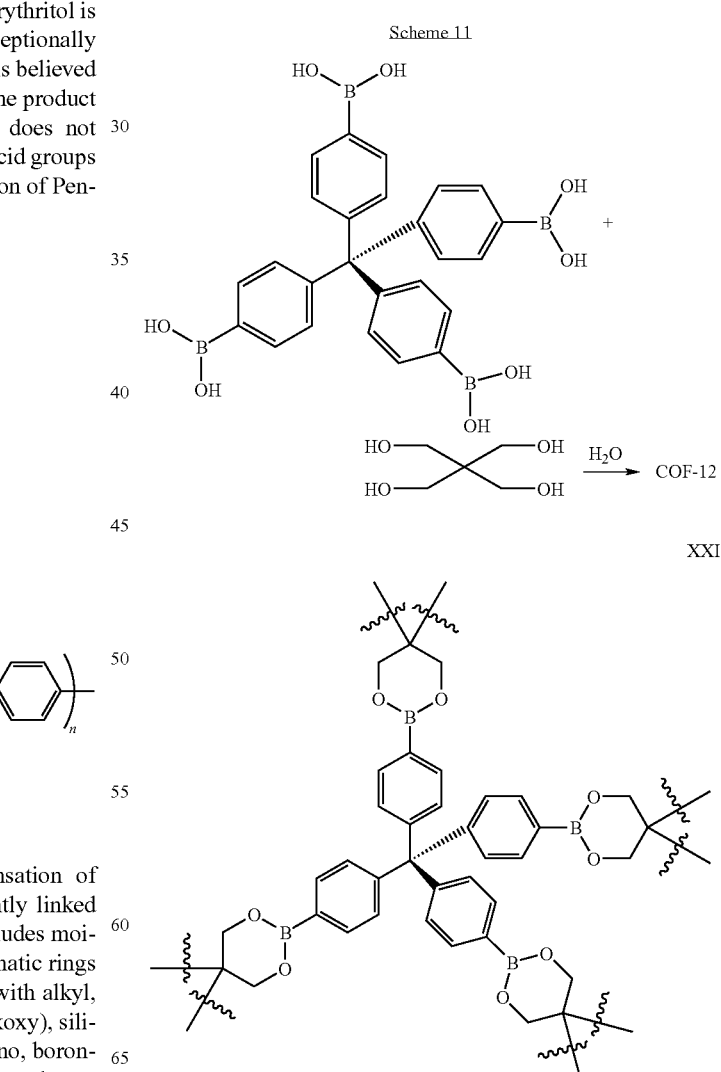

In another variation of the method of the invention, the known reaction of organo-borondichloride derivatives with boronic acid and with silyated amines to yield borazines is extended. Extension of this methodology to attain borazine COFs provides stable materials owing to the aromaticity of the borazine ring. Organo-borondichloride building blocks can be convenient using simple and high-yielding chemistry via boronic acid building blocks; amine reagents are commercially available. An attractive feature of borazine COFs are the ready points of derivatization provided by the wide availability R-groups for amine reagents. These reactions are normally carded out in apolar organic solvents at various temperatures.

Scheme 12

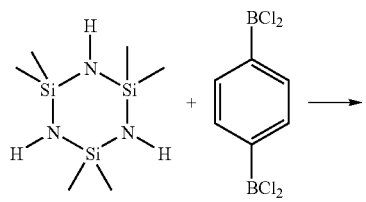

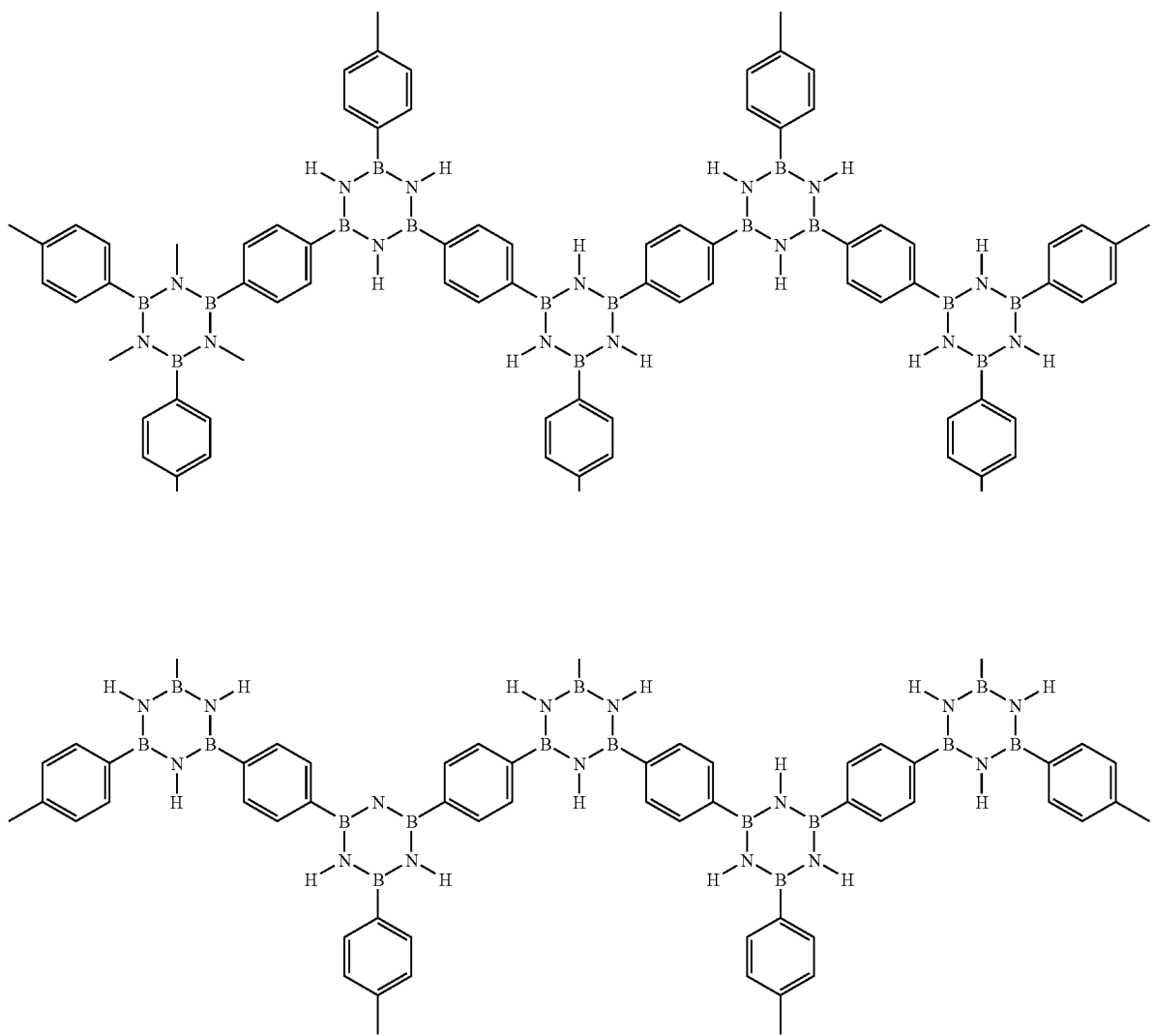

Again, each of the aromatic rings in Scheme 12 are optionally substituted with alkyl, OH, alkoxy, sulfur-containing groups (e.g., thioalkoxy), silicon-containing groups, halogen, nitro, amino, cyano, boron-containing groups, phosphorus-containing groups, carboxylic acids, or esters.

The following non-limiting examples illustrate the various embodiments of the present invention. Those skilled in the art will recognize many variations that are within the spirit of the present invention and scope of the claims.

I. Synthesis of Covalently Linked Organic Frameworks

The bisboronic acid starting materials used in the methods of the invention are commercially available, or can be easily synthesized. Moreover, the synthetic approach of the invention can be extended to a variety of boronic acids and esters with two or more functionalities. Boroxine rings, for example, act as trigonal building units and the organic linking groups, with two or more points of attachment, serves to link these into a network. Examples of suitable linking groups are set forth above, and may be derived from aromatic, aliphatic, multitopic and substituted boronic acids and esters. Use of a diverse array of linking groups enables the formation of specifically designed materials of differing molecular architectures.

Thermal gravimetric analysis (TGA) of boronic acid starting materials revealed that the observed weight loss is in accordance with the calculated amount of water produced after boroxine ring formation. This value is 21.52 wt. % (21.72 calc.) for XVII, and 14.10 wt. % (14.89 calc.) for XVIII.

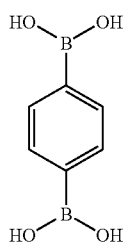

XVII

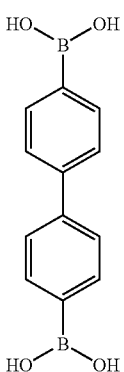

XVIII

Several methods of attaining the desired extended organic framework through the homo-polymerization of XVII are explored, and are summarized in Table 1.

TABLE 1

Characterization of 1,4-phenylenebisboronic acid polymerizations

| Method | PXRD (Å) | Activation | $N_2$ sorption (77 K) |
|---|---|---|---|
| Solid-state | amorphous | as synthesized | nonporous |
| DMF | 12.1, 10.3, 8.6, 7.4, 6.0 | as synthesized | nonporous |
| Toluene | 12.4, 10.9, and 7.5 | — | — |
| THF | 12.2 and 3.3 | acetone wash | nonporous |
| Triglyme | 12.8 and 3.3 | acetone wash | SA = 591 m$^2$/g |

EXAMPLE 1

Condensation of 1,4-phenylene bisboronic Acid Homo-polymerization a) Solid-state synthesis. When compound XVII is heated to 238° C. under vacuum (92 mtorr) for one day, the resulting white powder is amorphous by PXRD, and nonporous by low-pressure gravimetric nitrogen sorption (T=77 K). This lack of crystallinity and pore accessibility may indicate the need of a space-filling substance (e.g. solvent) during the synthesis around which the desired product may form.

b) Solvent-based syntheses. A saturated solution of compound XVII in DMF is heated to dryness, the as-synthesized material is nonporous by low-pressure gravimetric nitrogen sorption (T=77 K). The lack of porosity may be due to DMF molecules tightly bound to the framework within the pores. Although, activation methods such as washing with volatile solvent or evacuation under mild heating may lead to porous materials, X-ray diffraction shows such materials in general to be crystalline.

After heating a solution of XVII in THF and triglyme, or a suspension of XVII in toluene to 170° C. for 2.5 days, the fine powders are filtered and washed with acetone. The resulting products give rise to new low-angle peaks in the powder X-ray diffraction patterns (FIG. 1). Some starting material remains in the case of toluene, where the compound with formula XVII is not completely soluble.

EXAMPLE 2

Alternative Synthesis of COF-1

A Pyrex tube measuring o.d.×i.d.=10×8 mm$^2$ is charged with 1,4-benzene diboronic acid (BDBA) (25 mg, 0.15 mmol, Aldrich) and 1 mL of a 1:1 v:v solution of mesitylene:dioxane. The tube is flash frozen at 77 K (LN2 bath), evacuated to an internal pressure of 150 mtorr and flame sealed. Upon sealing the length of the tube is reduced to 18 cm. The reaction mixture is heated at 120 $^2$C for 72 h yielding a white solid at the bottom of the tube which is isolated by filtration and washed with acetone (30 mL). Yield: 17 mg, 71% for $(C_3H_2BO)_6 \cdot (C_9H_{12})_1$. Anal. Calcd. For $(C_3H_2BO)_6 \cdot (C_9H_{12})_1$: C, 63.79; H, 4.77. Found: C, 56.76; H, 4.34. Following guest S2 removal: Anal. Calcd. for $C_3H_2BO$: C, 55.56; H, 3.10. Found: C, 51.26; H, 2.91. Note: organoboron compounds typically give lowered carbon values in elemental microanalysis due to the formation of non-combustible boron carbide by-products.

EXAMPLE 3

Synthesis of COF-5

A Pyrex tube measuring o.d.xi.d.=10×8 mm$^2$ is charged with 1,4-benzene diboronic acid (BDBA) (25 mg, 0.15 mmol, Aldrich), 2,3,6,7,10,11-hexahydroxytriphenylene [(HHTP) 16 mg, 0.050 mmol, TCI] and 1 mL of a 1:1 v:v solution of mesitylene:dioxane. The tube is flash frozen at 77 K (LN2 bath) and evacuated to an internal pressure of 150 mtorr and flame sealed. Upon sealing the length of the tube is reduced to 18 cm. The reaction mixture is heated at 100° C. for 72 h to yield a free flowing gray-purple powder. Note that the purple color arises from oxidation of a small fraction HHTP which exhibits a very large extinction coefficient and is therefore very highly colored. This side product becomes incorporated within the pores imparting the purple color to the 'as synthesized' form of COF-5. Following guest removal (see adsorption results below) COF-5 is obtained as a light gray solid. Yield: 15 mg, 73% for $C_9H_4BO_2$ following guest removal. Anal. Calcld. for $C_9H_4BO_2$: C, 69.67; H, 2.60. Found: C, 66.48; H, 2.81. Note: organoboron compounds typically give lowered carbon values in elemental microanalysis due to the formation of noncombustible boron carbide by-products. No evidence for the formation of COF-1 is observed. Note that reaction of BDBA alone at 100° C. to form COF-1 is slow where after 168 h COF-1 it is obtained in only 25% yield.

II. Adsorption Analysis

Activation of samples for gas adsorption measurements. COF-1: A 50 mg sample of COF-1 is heated to 150° C. under dynamic vacuum for 12 h. The sample is backfilled with nitrogen and then transferred in an air atmosphere to the required vessel for gas adsorption measurements. COF-5: A 50 mg sample of COF-5 is placed in a 5 mL glass vial which is subsequently filled with HPLC grade (Aldrich) acetone. After 2 hours of exchange at room temperature the majority of the now yellow-purple acetone phase is decanted and the vial refreshed with acetone. After 12 hours the solvent is decanted again and the solid washed with acetone (3×3 mL) and left to air dry in a desiccator ($CaSO_4$) for 2 hours and then evacuated for 12 h under dynamic vacuum at ambient temperature. Following evacuation, the sample is back-filled with nitrogen and then transferred in an air atmosphere to the required vessel for gas adsorption measurements.

1. Sorption Experiments for Example 1

Gas sorption measurements are conducted in order to measure the accessible pore volume of the materials produced. The nitrogen gas sorption isotherms measured for products produced from solid state and DMF or THF synthetic conditions reveal the low accessible void volume of these materials (FIG. 2a). The isotherm measured for the product produced from triglyme, however, shows that it has a rigid framework, and can maintain its porosity in the absence of guests. An exact amount of the triglyme product is introduced into the microbalance apparatus and evacuated at room temperature to 10$^{-3}$ torr, according to an already published protocol. (Eddaoudi, M.; Li, H.; Yaghi, O. M. J. Am. Chem. Soc. 2000, 122, 1391-1397). The nitrogen gas sorption isotherm reveals reversible type I behavior characterized by a plateau reached at low relative pressure, which is indicative of sorption in monodisperse micropores contained in a robust framework (FIG. 2b).

The nitrogen apparent Langmuir surface area for the triglyme product is calculated to be 591 m$^2$/g (P/P$_0$=0.102). Recently reported PIMs have surface areas ranging 430-850 m$^2$/g, but marked hysteresis at low pressures is also observed. The same broad hysteresis spreading over the whole region of relative nitrogen pressures has been observed in other porous polymer materials studied in the past, including polyphenylene oxide polymers. (Ilinitch, O. M.; Fenelonov, V. B.; Lapkin, A. A.; Okkel, L. G.; Terskikh, V. V.; Zamaraev, K. I. Microporous and Mesoporous Materials, 1999, 31, 97-110). The cause has been assigned to swelling (intercalation) of a microporous sorbent by the sorbate or to the presence of mesopores accessible only through micropores. The importance of permanent porosity (the lack of framework deformation in the presence and absence of guest species) within a material is crucial to maintain performance over many cycles of use in future applications.

2. Sorption Experiments for Examples 2 and 3

With reference to FIGS. 3, 4, 5 and 6, gas adsorption isotherms are measured volumetrically using a Quantachrome Autosorb-1 automated adsorption analyzer. A liquid nitrogen bath (77 K) is used for $N_2$ isotherms and an argon bath (87 K) is used for Ar isotherms. Micropore sorption data using $CO_2$ are collected a 273 K (ice water bath). The $N_2$, Ar, and $CO_2$ gases used are UHP grade. For all isotherm plots, closed circles are used for adsorption data points and open circles are used to indicate desorption data points. With reference to FIGS. 7, 8, 9, and 10, the BET method is applied for measurement of the specific surface areas (As, m$^2$/g). In general, measured uptakes from Ar isotherms are slightly higher than for $N_2$, however the more conservative $N_2$ data for surface areas and pore volumes are provided herein. The higher uptakes for Ar are likely do to its small size which allows more adatoms to bind into adsorption sites in the frameworks that are too small to accommodate nitrogen.

The architectural stability and porosity of COF-1 and COF-5 are confirmed by measuring the nitrogen gas adsorption of the guest-free material. A sample of synthesized COF-1 is evacuated with a dynamic pressure of 10$^{-5}$ Torr vacuum and heated to 150° C. for 12 h to remove all the guests. This sample is used for measurement of the nitrogen isotherm at 77 K from 0-1 bar (1 bar=Po) which shows a very sharp uptake from P/Po=10$^{-5}$-10$^{-1}$, a signature feature of a microporous material (FIG. 3). The Brunauer-Emmett-Teller (BET) model is applied to the isotherm between P/P$_o$=0.04-0.1, resulting in an apparent surface area of SBET=711 m$^2$ g$^{-1}$; the pore volume V$_p$=0.32 cm$^3$g$^{-1}$ at P/P$_o$=0.90. These values surpass those of other layered materials including graphite (10 m$^2$g$^{-1}$), clays (10-100 m$^2$g$^{-1}$), and pillared clays (50-300 m$^2$g$^{-1}$) and are in the range of the most porous zeolites and many porous carbons. At higher pressures a slow rise in the isotherm occurs due to the existence of a small population of external mesopores between the crystallites; this is not uncommon for particles having platelet morphologies. The total surface area is calculated to be 711 m$^2$g$^{-1}$ with a micropore contribution of 587 m$^2$g$^{-1}$ (83%) and mesopore contribution of 124 m$^2$g$^{-1}$ (17%) from t-plot analysis. Argon and high-temperature carbon dioxide isotherms collected in the same pressure range are used to fit Density Functional Theory (DFT) models which account for the microscopic behavior of sorbed molecules. From these calculations a very reliable pore size distribution can be calculated and is shown (FIG. 3 inset). Corroborating the results from t-plot analysis (FIG. 11), the distribution is largely populated between 6 and 12 Å matching the micropore dimensions expected from the structure of COF-1, the range from 28-44 Å arises from the aforementioned interparticle mesopores. The cumulative pore volume (0.34 cm$^3$g$^{-1}$) and surface area (640 m$^2$g$^{-1}$) from DFT calculations compare favorably with the values determined above. Significantly, the isotherm for COF-1 is fully reversible and reproducible—a feature of stable materials whose structures exhibit permanent porosity. The nitrogen adsorption isotherm of COF-5 is measured under the same conditions as COF-1. It shows a reversible Type IV isotherm characteristic of mesoporous materials (FIG. 4). There are two notable features in this isotherm. The first is a sharp step observed for pore condensation between P/Po=0.11-0.15 caused by a narrow distribution of mesopores; this is supported by DFT calculations with a pore width of 27 Å dominating the distribution (FIG. 4 inset). Secondly, the absence of hysteresis during desorption is a common feature of materials containing hexagonally aligned one-dimensional mesopores with widths <40 Å. It is also apparent from the pore size distribution that 23% of the total surface area can be assigned to micropore uptake. Since an impurity phase has not been encountered, it is speculated that the origin of the significant low pressure uptake arises from partially slipped organic sheets that create grottos along the mesopore walls where adsorbate molecules are more strongly bound. The BET surface area of COF-5 is found to be 1,590 $m^2g^{-1}$, corresponding to a mesopore volume of 0.998 $cm^3g^{-1}$, values which are greater than double that reported for 26 Å MCM-41 materials (680 $m^2g^{-1}$, 0.26 $cm^3g^{-1}$) and exceed that of the highest reported surface area of 1,300 $m^2g^{-1}$ for a macroporous ordered silica.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A covalently linked organic network comprising:
a plurality of boron-containing clusters having the following formula:

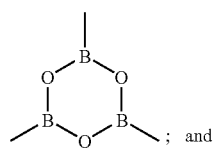

; and a plurality of linking groups that link the boron-containing clusters together, each linking group bonded to at least two distinct boron-containing clusters, the plurality of linking groups include a linking group described by Formula V-X:

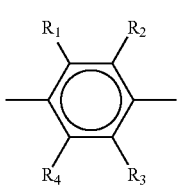

V

-continued

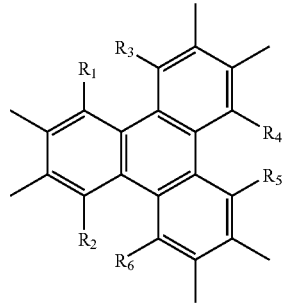

VI

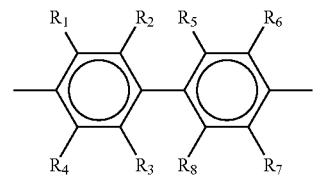

VII

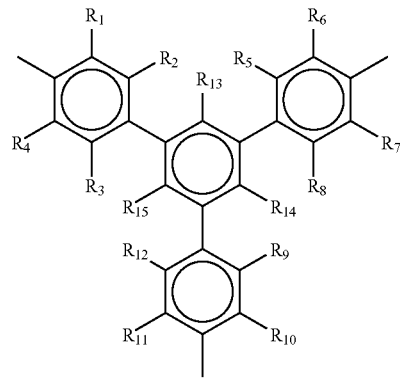

VIII

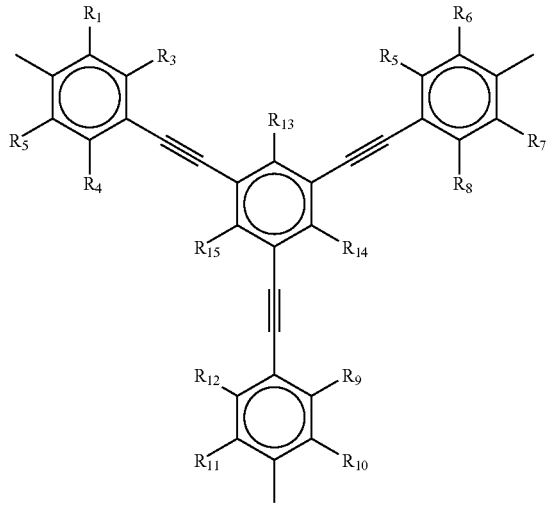

IX

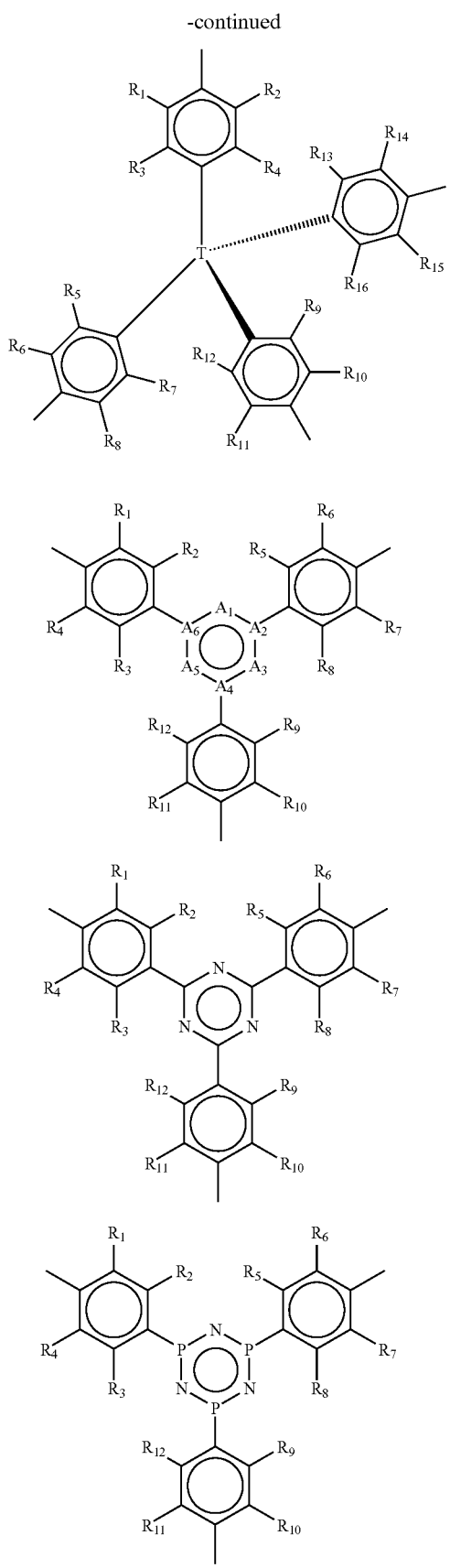

wherein:

R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, and R$_{16}$ are each independently H, alkyl, OH, alkoxy, sulfur-containing groups, silicon-containing groups, halogen, nitro, amino, cyano, boron-containing groups, phosphorus-containing groups, carboxylic acids, or esters and T is a tetrahedral atom or a tetrahedral group or cluster;

A$_1$, A$_2$, A$_3$, A$_4$, A$_5$, and A$_6$ are each independently absent or any atom or group capable of forming a sable ring structure; and wherein the plurality of boron-containing clusters and the plurality of linking groups are arranged to form either a covalently linked organic framework or a covalently linked organic polyhedron.

2. The covalently linked organic network of claim 1 wherein the plurality of boron-containing clusters comprises at least 10 boron-containing clusters.

3. The covalently linked organic network of claim 1 wherein the plurality of boron-containing clusters comprises at least 100 boron-containing clusters.

4. The covalently linked organic network of claim 1 wherein the plurality of linking groups comprises at least 10 linking groups.

5. The covalently linked organic network of claim 1 wherein the plurality of linking groups comprises at least 100 linking groups.

6. The covalently linked organic network of claim 1 wherein the boron-containing cluster includes a structure described by formula B$_x$Q$_y$C$_z$ wherein Q is oxygen, sulfur, nitrogen, or phosphorus; x and y are integers such that the valency of B is satisfied, and z is an integer from 0 to 6.

7. The covalently linked organic network of claim 1 wherein the surface area is from about 1 to about 20,000 m$^2$/g.

8. The covalently linked organic network of claim 1 made by the method comprising:

1) self condensation of a monomer having one or more boronic acid groups; or 2) reacting an aromatic polyalcohol with a compound having polyboronic acid groups.

9. A covalently linked organic network comprising:

a plurality of boron-containing clusters having the following formula

I and a plurality of linking groups that link the boron-containing clusters together, each linking group bonded to at least two distinct members of the plurality of boron-containing clusters the moiety described by Formula I, wherein the linking groups include a component selected from the group consisting of:

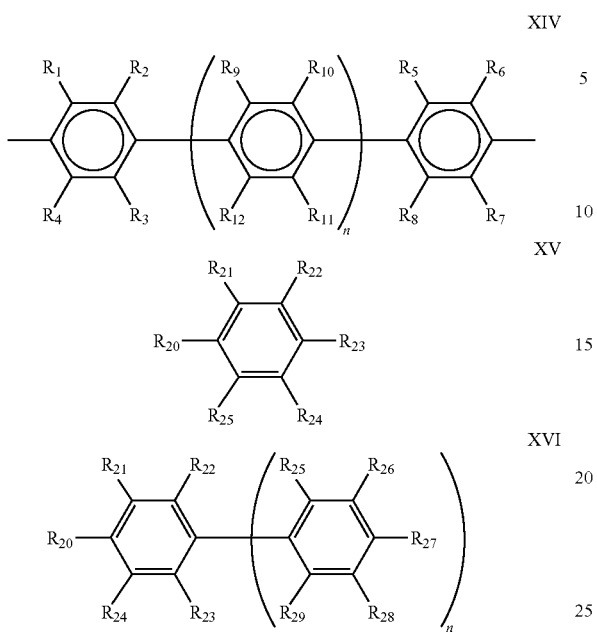

wherein:

R$_1$ through R$_{12}$ are each independently H, alkyl, OH, alkoxy, sulfur-containing groups, (e.g., thioalkoxy), silicon-containing groups, halogen, nitro, amino, cyano, boron-containing groups, phosphorus-containing groups, carboxylic acids, or esters R$_{20}$, R$_{21}$, R$_{22}$, R$_{23}$, R$_{24}$, and R$_{25}$ are each independently H, alkyl, OH, alkoxy, sulfur-containing groups (e.g., thioalkoxy), silicon-containing groups, halogen, nitro, amino, cyano, boron-containing groups, phosphorus-containing groups, carboxylic acids, esters, or a bond to a member from the plurality boron containing cluster with the provisio that formula XV at least two groups of R$_{20}$ to R$_{25}$ are bonds to two distinct members of the plurality of boron containing clusters and for formula XVI at least two groups of R$_{20}$ to R$_{29}$ are bonds to two distinct members of the plurality of boron containing clusters: and n is an integer greater than or equal to 1.

10. The covalently linked organic network of claim 9 wherein the plurality of boron-containing clusters comprises at least 10 boron-containing clusters.

11. The covalently linked organic network of claim 9 wherein the plurality of boron-containing clusters comprises at least 100 boron-containing clusters.

12. The covalently linked organic network of claim 9 wherein a portion of the plurality of linking groups comprise a linking group which forms a first bond with a first boron-containing cluster and a second bond with a second boron-containing cluster such that the angle between the first bond and the second bond is less than 180 degrees.

* * * * *

UNITED STATES PATENT AND TRADEMARK OFFICE
CERTIFICATE OF CORRECTION

PATENT NO. : 7,582,798 B2  Page 1 of 1
APPLICATION NO. : 11/256859
DATED : September 1, 2009
INVENTOR(S) : Yaghi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 114 days.

Signed and Sealed this

Fourteenth Day of September, 2010

David J. Kappos
*Director of the United States Patent and Trademark Office*